(12) United States Patent
Warshawsky et al.

(10) Patent No.: US 6,329,550 B1
(45) Date of Patent: Dec. 11, 2001

(54) AMIDOMALONAMIDES USEFUL AS INHIBITORS OF MMP OF MATRIX METALLOPROTEINASE

(75) Inventors: Alan M. Warshawsky, Carmel, IN (US); Michael J. Janusz, Oregonia, OH (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 09/464,907

(22) Filed: Dec. 17, 1999

Related U.S. Application Data

(60) Provisional application No. 60/172,246, filed on Dec. 31, 1998.

(51) Int. Cl.$^7$ .......................... C07C 233/05; A61K 31/16
(52) U.S. Cl. .......................... 564/153; 548/485; 548/486; 546/265; 514/332; 514/415; 514/616
(58) Field of Search ..................................... 564/153, 154; 514/616

(56) References Cited

U.S. PATENT DOCUMENTS 5,853,623   12/1998   Mohara et al. .

FOREIGN PATENT DOCUMENTS

| | | |
|---|---|---|
| 9506031 | 3/1995 | (WO) . |
| 9513289 | 5/1995 | (WO) . |
| 9519956 | 7/1995 | (WO) . |
| 9611209 | 4/1996 | (WO) . |
| 9616027 | 5/1996 | (WO) . |
| 9635712 | 5/1996 | (WO) . |
| 9703783 | 7/1996 | (WO) . |
| 9838179 | 2/1998 | (WO) . |

*Primary Examiner*—Shailendra Kumar
(74) *Attorney, Agent, or Firm*—Julie Anne Knight; Balaram Gupta; Eric K. Voelk

(57) ABSTRACT

The present application relates to novel aminomalonamides of the formula

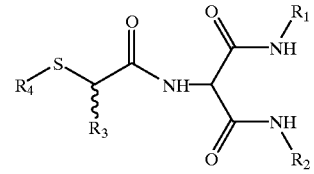

and pharmaceutical composition thereof which are useful for inhibiting matrix metalloproteinases.

34 Claims, No Drawings

AMIDOMALONAMIDES USEFUL AS INHIBITORS OF MMP OF MATRIX METALLOPROTEINASE

This application claims the benefit of Provisional Application No. 60/172,246 filed Dec. 31, 1998.

BACKGROUND OF THE INVENTION

The matrix metalloproteinases (MMPs) are a family of zinc containing endopeptidases which are capable of cleaving large biomolecules such as the collagens, proteoglycans and gelatins. Expression is upregulated by pro-inflammatory cytokines and/or growth factors. The MMP's are secreted as inactive zymogens which, upon activation, are subject to control by endogenous inhibitors, for example, tissue inhibitor of metalloproteinases (TIMP) and $\alpha_2$-macroglobulin. Chapman, K. T. et al., *J. Med. Chem.* 36, 4293–4301 (1993); Beckett, R. P. et al., *DDT* 1, 16–26 (1996). The characterizing feature of diseases involving the enzymes appears to be a stoichiometric imbalance between active enzymes and endogenous inhibitors, leading to excessive tissue disruption, and often degradation. McCachren, S. S., *Arthritis Rheum.* 34, 1085–1093 (1991).

The discovery of different families of matrix metalloproteinase, their relationships, and their individual characteristics have been categorized in several reports. Emonard, H. et al., *Cell Molec. Biol.* 36, 131–153 (1990); Birkedal-Hansen, H., *J. Oral Pathol.* 17, 445–451 (1988); Matrisian, L. M., *Trends Genet.* 6, 121–125 (1990); Murphy, G. J. P. et al., *FEBS Lett.* 289, 4–7 (1991); Matrisian, L. M., *Bioessays* 14, 455–463 (1992). Three groups of MMPs have been delineated: the collagenases which have triple helical interstitial collagen as a substrate, the gelatinases which are proteinases of denatured collagen and Type IV collagen, and the stromelysins which were originally characterized as proteoglycanases but have now been identified to have a broader proteolytic spectrum. Examples of specific collagenases include fibroblast collagenase characterized as proteoglycanases but have now been identified to have a broader proteolytic spectrum. Examples of specific collagenases include fibroblast collagenase (MMP-1), neutrophil collagenase (MMP-8), and collagenase 3 (MMP-13). Examples of gelatinases include 72 kDa gelatinase (gelatinase A; MMP-2) and 92 kDa gelatinase (gelatinase B; MMP-9). Examples of stromelysins include stromelysin 1 (MMP-3), stromelysin 2 (MMP-10) and matrilysin (MMP-7). Other MMPs which do not fit neatly into the above groups include metalloelastase (MMP-12), membrane-type MMP (MT-MMP or MMP-14) and stromelysin 3 (MMP-11). Beckett, R. P. et al., supra.

Over-expression and activation of MMPs have been linked with a wide range of diseases such as cancer; rheumatoid arthritis; osteoarthritis; chronic inflammatory disorders, such as emphysema and smoking-induced emphysema; cardiovascular disorders, such as atherosclerosis; corneal ulceration; dental diseases such as gingivitis and periodontal disease; and neurological disorders, such as multiple sclerosis. For example, in adenocarcinoma, invasive proximal gastric cells express the 72 kDa form of collagenase Type IV, whereas the noninvasive cells do not. Schwartz, G. K. et al., *Cancer* 73, 22–27 (1994). Rat embryo cells transformed by the Ha-ras and v-myc oncogenes or by Ha-ras alone are metastatic in nude mice and release the 92 kDa gelatinase/collagenase (MMP-9). Bernhard, E. J. et al., *Proc. Natl. Acad. Sci.* 91, 4293–4597 (1994). The plasma concentration of MMP-9 was significantly increased ($P<0.01$) in 122 patients with gastrointestinal tract cancer and breast cancer. Zucker, S. et al., *Cancer Res.* 53, 140–146 (1993). Moreover, intraperitoneal administration of batimastat, a synthetic MMP inhibitor, gave significant inhibition in the growth and metastatic spread and number of lung colonies which were produced by intravenous injection of the B16-BL6 murine melanoma in C57BL/6N mice. Chirivi, R. G. S. et al., *Int. J. Cancer* 58, 460–464 (1994). Over-expression of TIMP-2, the endogenous tissue inhibitor of MMP-2, markedly reduced melanoma growth in the skin of immunodeficient mice. Montgomery, A. M. P. et al., *Cancer Res.* 54, 5467–5473 (1994).

Accelerated breakdown of the extracellular matrix of articular cartilage is a key feature in the pathology of both rheumatoid arthritis and osteoarthritis. Current evidence suggests that the inappropriate synthesis of MMPs is the key event. Beeley, N. R. A. et al., *Curr. Opin. Ther. Patents,* 4(1), 7–16 (1994). The advent of reliable diagnostic tools have allowed a number of research groups to recognize that stromelysin is a key enzyme in both arthritis and joint trauma. Beeley, N. R. A. et al., *Id.*; Hasty, K. A. et al., *Arthr. Rheum.* 33, 388–397 (1990). It has also been shown that stromelysin is important for the conversion of procollagenase to active collagenase. Murphy, G. et al., *Biochem. J.* 248, 265–268 (1987).

Furthermore, a range of MMPs can hydrolyse the membrane-bound precursor of the pro-inflammatory cytokine tumor necrosis factor $\alpha$ (TNF-$\alpha$). Gearing, A. J. H. et al., *Nature* 370, 555–557 (1994). This cleavage yields mature soluble TNF-$\alpha$ and the inhibitors of MMPs can block production of TNF-$\alpha$ both in vitro and in vivo. Gearing, A. J. H. et al., Id.; Mohler, K. M. et al., *Nature* 370, 218–220 (1994); McGeehan, G. M. et al., *Nature* 370, 558–561 (1994). This pharmacological action is a probable contributor to the antiarthritic action of this class of compounds seen in animal models. Beckett, R. P. et al., supra.

Stromelysin has been observed to degrade the $\alpha_1$-proteinase inhibitor which regulates the activity of enzymes such as elastase, excesses of which have been linked to chronic inflammatory disorders such as emphysema and chronic bronchitis. Beeley, N. R. A. et al., supra.; Wahl, R. C. et al., *Annual Reports in Medicinal Chemistry* 25, 177–184 (1990). In addition, a recent study indicates that MMP-12 is required for the development of smoking-induced emphysema in mice. Science, 277, 2002 (1997). Inhibition of the appropriate MMP may thus potentiate the inhibitory activity of endogenous inhibitors of this type.

High levels of mRNA corresponding to stromelysin have been observed in atherosclerotic plaques removed from heart transplant patients. Henney, A. M., et al., *Proc. Natl. Acad. Sci.* 88, 8154–8158 (1991). It is submitted that the role of stromelysin in such plaques is to encourage rupture of the connective tissue matrix which encloses the plaque. This rupture is in turn thought to be a key event in the cascade which leads to clot formation of the type seen in coronary thrombosis. MMP inhibition is thus a preventive measure for such thromboses.

Collagenase, stromelysin and gelatinase have been implicated in the destruction of the extracellular matrix of the cornea. This is thought to be an important mechanism of morbidity and visual loss in a number of ulcerative ocular diseases, particularly those following infection or chemical damage. Burns, F. R. et al., *Invest. Opthalmol. and Visual Sci.* 32, 1569–1575 (1989). The MMPs present in the eye during ulceration are derived either endogenously from infiltrating leucocytes or fibroblasts, or exogenously from microbes.

Collagenase and stromelysin activities have been identified in fibroblasts isolated from inflamed gingiva and the levels of enzyme have been correlated with the severity of the gingivitis observed. Beeley, N. R. A. et al., supra.; Overall, C. M. et al., *J. Periodontal Res.* 22, 81–88 (1987).

Excessive levels of gelatinase-B in cerebrospinal fluid has been linked with incidence of multiple sclerosis and other neurological disorders. Beeley, N. R. A. et al., *supra.;* Miyazaki, K. et al., *Nature* 362, 839–841 (1993). The enzyme may play a key role in the demyelination of neurones and the breakdown of the blood brain barrier which occurs in such disorders.

SUMMARY OF THE INVENTION

The present invention provides novel aminomalonamides of the formula

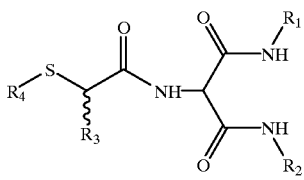

formula (1)

wherein
R$_1$ and R$_2$ are each independently selected from the group consisting of hydrogen, C$_1$–C$_{10}$ alkyl, —(CH$_2$)$_a$—Ar$_1$, and —(CH$_2$)$_b$—Ar$_2$; wherein
a is an integer from 1 to 6;
b is an integer from 2 to 6;
Ar$_1$ is a radical selected from the group consisting of

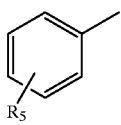 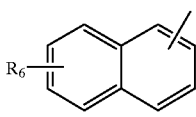 and 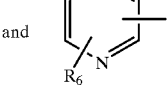

wherein R$_5$ is 1 or 2 substituents independently selected from the group consisting
of hydrogen, halogen, C$_1$–C$_4$ alkyl, hydroxy, and C$_1$–C$_4$ alkoxy;
R$_6$ is selected from the group consisting of hydrogen, halogen, C$_1$–C$_4$ alkyl, and C$_1$–C$_4$ alkoxy;
Ar$_2$ is the radical

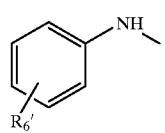

wherein
R$_{6'}$ is selected from the group consisting of hydrogen, halogen, C$_1$–C$_4$ alkyl, and C$_1$–C$_4$ alkoxy;
R$_3$ is selected from the group consisting of C$_1$–C$_6$ alkyl, —(CH$_2$)$_m$—W, —(CH$_2$)$_p$—Ar$_3$, —(CH$_2$)$_k$—CO$_2$R$_9$, —(CH$_2$)$_m$—NR$_8$, SO$_2$—Y$_1$, and —(CH$_2$)$_m$—Z—Q
wherein
m is an integer from 2 to 8;
p is an integer from 0–10;
k is an integer from 1 to 9;

W is phthalimido;
Ar$_3$ is selected from the group consisting of

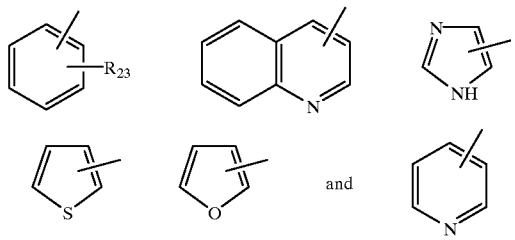

wherein
R$_{23}$ is from 1 to 2 substituents independently selected from the group consisting of hydrogen, halogen, C$_1$–C$_4$ alkyl, and C$_1$–C$_4$ alkoxy;
R$_{8'}$ is hydrogen or C$_1$–C$_6$ alkyl;
R$_9$ is hydrogen or C$_1$–C$_6$ alkyl;
Y$_1$ is selected from the group consisting of hydrogen, —(CH$_2$)$_j$—Ar$_4$, and —N(R$_{24}$)$_2$ wherein
j is 0 or 1;
R$_{24}$ each time selected is independently hydrogen or C$_1$–C$_6$ alkyl or are taken together with the nitrogen to which they are attached to form N-morpholino, N-piperidino, N-pyrrolidino, or N-isoindolyl;
Ar$_4$ is the radical

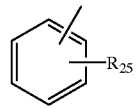

wherein
R$_{25}$ is from 1 to 3 substituents independently selected from the group consisting of hydrogen, halogen, C$_1$–C$_4$ alkyl, and C$_1$–C$_4$ alkoxy;
Z is selected from the group consisting of —O—, —NR$_8$—, —C(O)NR$_8$—, —NR$_8$C(O)—, —NR$_8$C(O)NH—, —NR$_8$C(O)O—, and —OC(O)NH—; wherein
R$_8$ is hydrogen or C$_1$–C$_6$ alkyl;
Q is selected from the group consisting of hydrogen, —(CH$_2$)$_n$—Y$_2$, and —(CH$_2$)$_x$Y$_3$; wherein
n is an integer from 0 to 4;
Y$_2$ is selected from the group consisting of hydrogen, —(CH$_2$)$_h$—Ar$_5$ and —(CH$_2$)$_t$—C(O)OR$_{27}$ wherein
Ar$_5$ is selected from the group consisting of

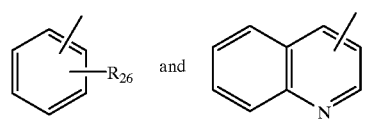

wherein
R$_{26}$ is from 1 to 3 substituents independently selected from the group consisting of hydrogen, halogen, C$_1$–C$_4$ alkyl, and C$_1$–C$_4$ alkoxy;
h is an integer from 0 to 6;
t is an integer from 1 to 6;
R$_{27}$ is hydrogen or C$_1$–C$_6$ alkyl;
x is an integer from 2 to 4;
Y$_3$ is selected from the group consisting of —N(R$_{28}$)$_2$, N-morpholino, N-piperidino, N-pyrrolidino, and N-isoindolyl; wherein $R_{28}$ each time taken is independently hydrogen or $C_1$–$C_6$ alkyl;

$R_4$ is selected from the group consisting of hydrogen, —C(O)$R_{10}$, —C(O)—(CH$_2$)$_q$—K and —S—G wherein
$R_{10}$ is selected from the group consisting of hydrogen, $C_1$–$C_4$ alkyl, phenyl, and benzyl;
q is 0, 1, or 2;
K is selected from the group consisting of

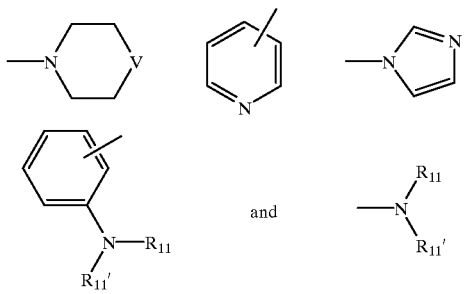

wherein
V is selected from the group consisting of a bond, —CH$_2$—, —O—, —S(O)$_r$—, —NR—, and —NC(O)R'—; wherein
r is 0, 1, or 2;
R is selected from the group consisting of hydrogen, $C_1$–$C_4$ alkyl, and benzyl;
R' is selected from the group consisting of hydrogen, —CF$_3$, $C_1$–$C_{10}$ alkyl, phenyl, and benzyl;
$R_{11}$ is selected from the group consisting of hydrogen, $C_1$–$C_4$ alkyl, and benzyl;
$R_{11'}$ is selected from the group consisting of hydrogen, $C_1$–$C_4$ alkyl, and benzyl;
G is selected from the group consisting of

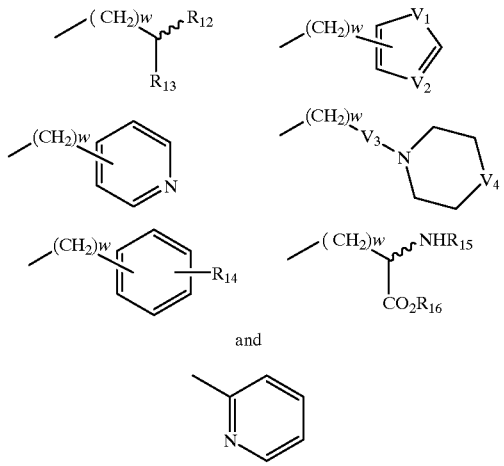

wherein
w is an integer from 1 to 3;
$R_{12}$ is selected from the group consisting of hydrogen, $C_1$–$C_6$ alkyl, —CH$_2$CH$_2$S(O)$_e$CH$_3$, and benzyl; wherein e is 0, 1, or 2;
$R_{13}$ is selected from the group consisting of hydrogen, hydroxy, amnino, $C_1$–$C_6$ alkyl, N-methylamino, N,N-dimethylamino, —CO$_2$R$_{17}$, and —OC(O)R$_{18}$; wherein
$R_{17}$ is hydrogen, —CH$_2$O—C(O)C(CH$_3$)$_3$, $C_1$–$C_4$ alkyl, benzyl, or diphenylmethyl;

$R_{18}$ is hydrogen, $C_1$–$C_6$ alkyl or phenyl;
$R_{14}$ is 1 or 2 substituents independently selected from the group consisting of hydrogen, $C_1$–$C_4$ alkyl, $C_1$–$C_4$ alkoxy, or halogen;
$V_1$ is selected from the group consisting of —O—, —S—, and —NH—;
$V_2$ is selected from the group consisting of —N— and —CH—;
$V_3$ is selected from the group consisting of a bond and —C(O)—;
$V_4$ is selected from the group consisting of —O—, —S—, —NR$_{19}$—, and —NC(O)R$_{20}$—; wherein
$R_{19}$ is hydrogen, $C_1$–$C_4$ alkyl, or benzyl;
$R_{20}$ is hydrogen, —CF$_3$, $C_1$–$C_{10}$ alkyl, or benzyl;
$R_{15}$ is selected from the group consisting of hydrogen, $C_1$–$C_6$ alkyl and benzyl;
$R_6$ is selected from the group consisting of hydrogen and $C_1$–$C_4$ alkyl; and stereoisomers, pharmaceutically acceptable salt, and hydrate thereof.

The present invention further provides a method of inhibiting matrix metalloproteinases (MMPs) in a patient in need thereof comprising administering to the patient an effective matrix metalloproteinase inhibiting amount of a compound of formula (1). As such the present invention provides a method of treating a neoplastic disease state or cancer; rheumatoid arthritis; osteoarthritis; osteoporosis; cardiovascular disorders, such as atherosclerosis; corneal ulceration; dental diseases, such as gingivitis or periodontal disease; and neurological disorders, such as multiple sclerosis; chronic inflammatory disorders, such as emphysema and especially smoking-induced emphysema.

In addition, the present invention provides a composition comprising an assayable amount of a compound of formula (1) in admixture or otherwise in association with an inert carrier. The present invention also provides a pharmaceutical composition comprising an effective MMP inhibitory amount of a compound of formula (1) in admixture or otherwise in association with one or more pharmaceutically acceptable carriers or excipients.

As used in this application:
a) the term "halogen" refers to a fluorine atom, chlorine atom, bromine atom, or iodine atom;
b) the term "$C_1$–$C_6$ alkyl" refers to a branched or straight chained alkyl radical containing from 1 to 6 carbon atoms, such as methyl, ethyl, n-propyl, isopropyl, n-butyl, isobutyl, t-butyl, pentyl, hexyl, etc.;
c) the term "$C_1$–$C_4$ alkyl" refers to a saturated straight or branched chain alkyl group containing from 1 to 4 carbon atoms and includes methyl, ethyl, propyl, isopropyl, n-butyl, s-butyl, isobutyl, and t-butyl;
d) the term "$C_1$–$C_4$ alkoxy" refers to a straight or branched alkoxy group containing from 1 to 4 carbon atoms, such as methoxy, ethoxy, n-propoxy, isopropoxy, n-butoxy, isobutoxy, t-butoxy, etc.;
e) the term "$C_1$–$C_{10}$ alkyl" refers to a saturated straight or branched chained alkyl group containing from 1 to 10 carbon atoms and includes methyl, ethyl, n-propyl, isopropyl, n-butyl, isobutyl, t-butyl, pentyl, hexyl, heptyl, octyl, nonyl, and decyl, etc.;
f) as used in the examples and preparations, the following terms have the meanings indicated: "g" refers to grams, "mg" refers to milligrams, "µg" refers to micrograms, "mol" refers to moles, "mmol" refers to millimoles, "nmole" refers to nanomoles, "L" refers to liters, "mL" or "ml" refers to milliliters, "µL" refers to microliters, "° C." refers to degrees Celsius, "$R_f$" refers to retention factor, "mp" refers to melting point, "dec" refers to decomposition, "bp" refers to boiling point, "mm of Hg" refers to pressure in millimeters of mercury, "cm" refers to centimeters, "nm" refers to nanometers, "brine" refers to a saturated aqueous sodium chloride solution, "M" refers to molar, "mM" refers to millimolar, "$\mu$M" refers to micromolar, "nM" refers to nanomolar, "HPLC" refers to high performance liquid chromatography, "HRMS" refers to high resolution mass spectrum, "DMF" refers to dimethylformamide, "$\mu$Ci" refers to microcuries, "i.p." refers to intraperitoneally, "i.v." refers to intravenously, and "DPM" refers to disintegrations per minute;

g) the term "pharmaceutically acceptable salts" refers to either an acid addition salt or a basic addition salt.

The expression "pharmaceutically acceptable acid addition salts" is intended to apply to any non-toxic organic or inorganic acid addition salt of the base compounds represented by formula (1) or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

The expression "pharmaceutically acceptable basic addition salts" is intended to apply to any non-toxic organic or inorganic basic addition salts of the compounds represented by formula (1) or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

As is appreciated by one of ordinary skill in the art the compounds of formula (1) exist as stereoisomers. Specifically, it is recognized that they exist as stereoisomers at the point of attachment of the substituents $R_3$, $R_{12}$, and —$NHR_{15}$. Where indicated the compounds of this application, whether of formula (1), starting materials, or intermediates, follow either the (+)- and (−)-designation for optical rotation, the (D)- and (L)-designation of relative stereochemistry, or the Cahn-Ingold-Prelog designation of (R)- and (S)-for the stereochemistry. Any reference in this application to one of the compounds of the formula (1) is meant to encompass either specific stereoisomers or a mixture of stereoisomers.

The specific stereoisomers can be prepared by stereospecific synthesis using enantiomerically pure or enantiomerically enriched starting materials which are well known in the art. The specific stereoisomers of amino acid starting materials are commercially available or can be prepared by stereospecific synthesis as is well known in the art or analogously known in the art, such as D. A. Evans, et al. *J. Am. Chem. Soc.*, 112, 4011–4030 (1990); S. Ikegami et al. *Tetrahedron*, 44, 5333–5342 (1988); W. Oppolzer et al. *Tet. Lets.* 30, 6009–6010 (1989); *Synthesis of Optically Active α-Amino-Acids*, R. M. Williams (Pergamon Press, Oxford 1989); M. J. O'Donnell ed.: α-*Amino-Acid Synthesis*, Tetrahedron Symposia in print, No. 33, *Tetrahedron* 44, No. 17 (1988); U. Schöllkopf, *PureAppl. Chem.* 55, 1799 (1983); U. Hengartner et al. *J. Org. Chem.*, 44, 3748–3752 (1979); M. J. O'Donnell et al. *Tet. Lets.*, 2641–2644 (1978); M. J. O'Donnell et al. *Tet. Lets.* 23, 4255–4258 (1982); M. J. O'Donnell et al. *J. Am. Chem. Soc.*, 110, 8520–8525 (1988).

The specific stereoisomers of either starting materials or products can be resolved and recovered by techniques known in the art, such as chromatography on chiral stationary phases, enzymatic resolution, or fractional recrystallization of addition salts formed by reagents used for that purpose. Useful methods of resolving and recovering specific stereoisomers are known in the art and described in *Stereochemistry of Organic Compounds*, E. L. Eliel and S. H. Wilen, Wiley (1994) and *Enantiomers, Racemates, and Resolutions*, J. Jacques, A. Collet, and S. H. Wilen, Wiley (1981).

As with any group of structurally related compounds which possess a particular utility, certain groups and configurations of substituents are preferred for the compounds of formula (1). Preferred embodiments are given below:

The compounds in which $R_1$ and $R_2$ are selected from the group consisting of $C_1$–$C_6$ alkyl and —$(CH_2)_a$—$Ar_1$ are preferred;

The compounds in which $R_1$ and $R_2$ are —$(CH_2)_a$—$Ar_1$ are more preferred;

The compounds in which $R_1$ and $R_2$ are —$(CH_2)_a$—$Ar_1$ in which a is 1 or 2 and $Ar_1$ is phenyl or substituted phenyl are most preferred;

The compounds in which $R_3$ is selected from the group consisting of $C_1$–$C_6$ alkyl and —$(CH_2)_p$—$Ar_3$ are preferred;

Compounds in which $R_4$ is selected from the group consisting of hydrogen, —$C(O)R_{10}$ and —S—G are preferred;

Compounds in which $R_4$ is hydrogen are more preferred; and

Compounds in which $R_4$ is selected from the group consisting of —$C(O)R_{10}$ and $R_{10}$ is $C_1$–$C_4$ alkyl more preferred.

Examples of compounds encompassed by the present invention include the following. It is understood that the examples encompass all of the isomers of the compound and mixtures thereof. This list is meant to be representative only and is not intended to limit the scope of the invention in any way:

N,N'-di-(3-diphenylpropyl)-2-((S)-2-mercapto-4-phenylbutryrylamino)malonamide;

N,N'-di-(4-diphenylbutyl)-2-((S)-2-mercapto-4-phenylpropionylamino)malonamide; and N,N'-di-(3-diphenylpropyl)-2-((S)-2-mercapto-4-phenylbutyrylamino)malonamide.

The compounds of formula (1) can be prepared by utilizing techniques and procedures well known and appreciated by one of ordinary skill in the art. To illustrate, general synthetic schemes for preparing intermediates and the compounds of formula (1) are set forth below. In the reaction schemes below, the reagents and starting materials are readily available to one of ordinary skill in the art and all substituents are as

Reaction Scheme A

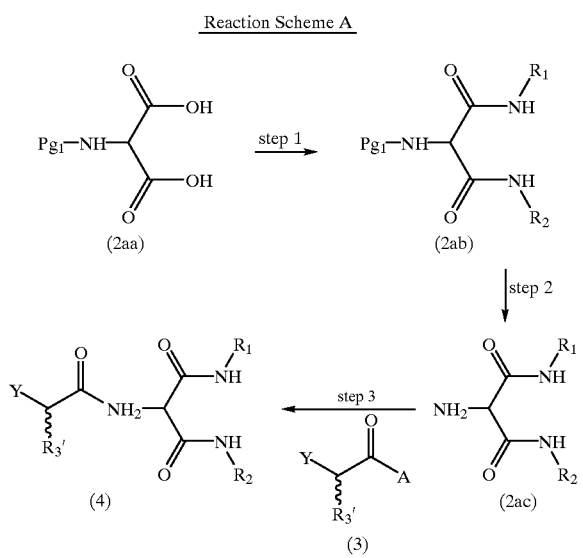

previously defined unless otherwise indicated.

In Scheme A, step 1, an appropriate protected aminomalonic acid derivative of the formula (2aa) is coupled with an appropriate amine to give a compound of formula (2ab). An appropriate protected aminomalonic acid derivative of the formula (2aa) is one in which the protecting group, $Pg_1$, can be removed in the presence of the amide formed in this step. The use of t-Boc for $Pg_1$ is preferred.

Such an appropriate amino protected aminomalonic acid derivatives are readily prepared by amine protecting diethyl aminomalonate followed by ester hydrolysis. An appropriate amine is one which gives rise to $R_1$ and $R_2$ as desired in the final product of formula (1). As is appreciated by the person skilled in the art, compounds of formula (1) in which $R_1$ and $R_2$ are different can be prepared by using mono-carboxy protected aminomalonic acid derivatives using this step, followed by selective removal of the carboxy protecting group and repeated amide formation to give compounds o formula (2ab) in which $R_1$ and $R_2$ are different.

Such coupling reactions to form amides are carried out in suitable solvents, such as dichloromethane, tetrahydrofuran, diethyl ether, chloroform, and the like, and using suitable bases, such as triethylamine, N-methylmorpholine, N,N-diisopropylethylamine, pyridine, and the like, and coupling reagents, as required, and are well known and appreciated in the art. The reactions are generally carried out at −10° C. to the refluxing temperature of the solvent and generally require form 1 hour to 2 days. The product can be isolated and purified by techniques well known in the art, such as extraction, evaporation, trituration, lyophilization, chromatography, and recrystallization.

The selection of an appropriate coupling reagent is within the skill of the art. Particularly suitable coupling reagents include 1-ethyl-3-(3-(dimethylamino)propyl)carbodiimide and 1-hydroxy-benzotriazole or N,N'-diisopropylcarbodiimide and 1-hydroxy-benzotriazole. Other coupling agents are benzotriazol-1-yloxytris(pyrrolidino)phosphonium hexafluorophosphate complex pyridine benzotriazol-1-yloxytris(dimethylamino) phosphonium hexafluorophosphate complex, carbodiimides (e.g., N,N'-dicyclohexylcarbodiimide); cyanamides (e.g., N,N-dibenzylcyanamide); (3) ketenimines; isoxazolium salts (e.g., N-ethyl-5-phenyl-isoxazolium-3'-sulfonate; monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; alkoxylated acetylene (e.g., ethoxyacetylene); reagents which form a mixed anhydride with the carboxyl moiety of the amino acid (e.g., ethylchloroformate and isobutylchloroformate). Other activating reagents and their use in peptide coupling are described by Kapoor, *J. Pharm. Sci.*, 59, 1–27 (1970).

In Reaction Scheme A, step 2, the amino protecting group, $Pg_1$, of the compound of formula (2ab) is selectively removed to give the compound of formula (2ac). Such selective amino deprotection reactions are well known and appreciated in the art. The product can be isolated and purified by techniques well known in the art, such as extraction, evaporation, salt formation, trituration, lyophilization, chromatography, and recrystallization.

In Reaction Scheme A, step 3, a compound of formula (2ac) coupled with an appropriate acid derivative bearing $R_{3'}$ and Y (compound of formula (3)) to give a compound of formula (4). Such coupling reactions are well known and appreciated in the art and discussed above. The product o can be isolated and purified by techniques well known in the art such as extraction, evaporation, salt formation, trituration, lyophilization, chromatography, and recrystallization.

An appropriate compound of formula (3) is one in which $R_{3'}$ is $R_3$ as desired in the final product of formula (1) or gives rise after deprotection to $R_3$ as desired in the final product of formula (1) and Y is a protected thio substituent or Y may be a protected hydroxy substituent or bromo which gives rise upon selective deprotection and displacement or displacement and further deprotection and/or elaboration, if required, to —$SR_4$ as desired in the final product of formula (1). Alternately, an appropriate compound of formula (3) may also be one in which $R_{3'}$ gives rise to $R_{3''}$ which, upon derivatization, gives rise $R_3$ as desired in the final product of formula (1) and Y is a protected thio substituent. In addition, an appropriate compound of formula (3) may also be one in which the stereochemistry at the $R_{3'}$ and Y bearing carbon is as desired in the final product of formula (1) or gives rise after displacement to the stereochemistry as desired at that carbon in the final product of formula (1). The activating group (A) is one which undergoes an amidation reaction. As is well known in the art an amidation reaction may proceed through an acid, A is —OH; or an acid may be first converted to an acid chloride, A is —Cl; or an activated intermediate; such as an anhydride; a mixed anhydride of aliphatic carboxylic acid, such as formic acid, acetic acid, propionic acid, butyric acid, isobutyric acid, pivalic acid, 2-ethylbutyric acid, trichloroacetic acid, trifluoroacetic acid, and the like; of aromatic carboxylic acids, such as benzoic acid and the like; of an activated ester, such as phenol ester, p-nitrophenol ester, 2,4-dinitrophenol ester, pentafluorophenol ester, pentachlorophenol ester, N-hydroxysuccinimide ester, N-hydroxyphthalimide ester, 1-hydroxy-1H-benztriazole ester, and the like; activated amide, such as imidazole, dimethylpyrazole, triazole, or tetrazole; or an intermediate formed in the presence of coupling agents, such as dicyclohexylcarbodiimide or 1-(3-dimethylaminopropyl)-3-ethylcarbodiimide. Acid chlorides and activated intermediates may be prepared but is not necessarily isolated before the addition of diethyl aminomalonate.

The use and selection of appropriate protecting groups is within the ability of those skilled in the art and will depend upon compound of formula (3) to be protected, the presence of other protected amino acid residues, other protecting groups, and the nature of the particular $R_3$ and/or $R_4$ group(s) ultimately being introduced. Compounds of formula (3) in which Y is bromo and protected thio are commercially available or can be prepared utilizing materials, techniques, and procedures well known and appreciated by one of ordinary skill in the art or described herein. See PCT Application WO 96/11209, published Apr. 18, 1996. Examples commercially available compounds of formula (3) in which Y is bromo include 2-bromopropionic acid, 2-bromobutyric acid, 2-bromovaleric acid, 2-bromohexanoic acid, 6-(benzoylamino)-2-bromohexanoic acid, 2-bromoheptanoic acid, 2-bromooctanoic acid, 2-bromo-3-methylbutyric acid, 2-bromoisocaproic acid, 2-bromo-3-(5-imidazoyl)proionic acid, (R)-(+)-2-bromopropionic acid, (S)-(−)-2-bromopropionic acid.

The compound of formula (4) can also be prepared as set forth below in Reaction Scheme B.

Reaction Scheme B

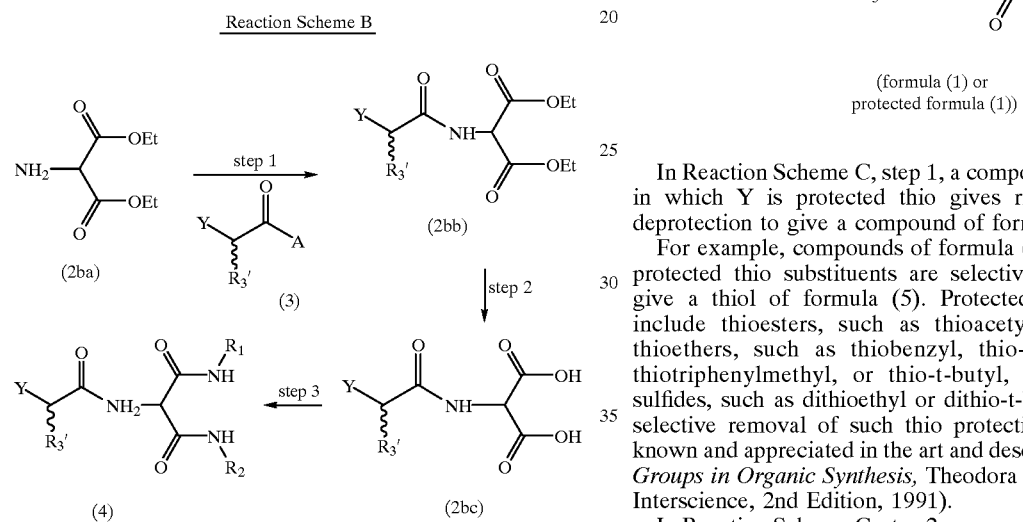

In Scheme B, step 1, diethyl aminomalonate (formula (2ba)) is coupled with an appropriate acid derivative of formula (3) to give a compound of formula (2bb). In Reaction Scheme B, an appropriate acid derivative of formula (3) is one in which $R_3'$ is as describe above in Reaciton Scheme A and Y is a protected thio group which is stable to the hydrolysis reaction of step 2. In Reaction Scheme B, the use of compoudns in which Y is p-methoxybenzylmercapto is preferred. Such coupling reactions are carried out in suitable solvents and using suitable bases and coupling agents, as required, and are well known and appreciated in the art and are discussed above.

In Reaction Scheme B, step 2, the compound of formula (2bb) is hydrolyzed to give a the diacid of formula (2bc). The hydrolysis of esters can be carried out under acidic or basic conditions as is well known in the art.

In Reaction Scheme B, step 3, a compound of formula (2bc) is coupled with a appropriate amine as described in Reaction Scheme A, step 1, above, to give a compound of formula (4).

In Reaction Scheme C a compound of formula (4) in which $R_{3'}$ is $R_3$ as desired in the final product of formula (1) or gives rise after deprotection to $R_3$ as desired in the final product of formula (1) and Y is a protected thio substituent or hydroxy or bromo gives rise to a final product of formula (1).

Reaction Scheme C

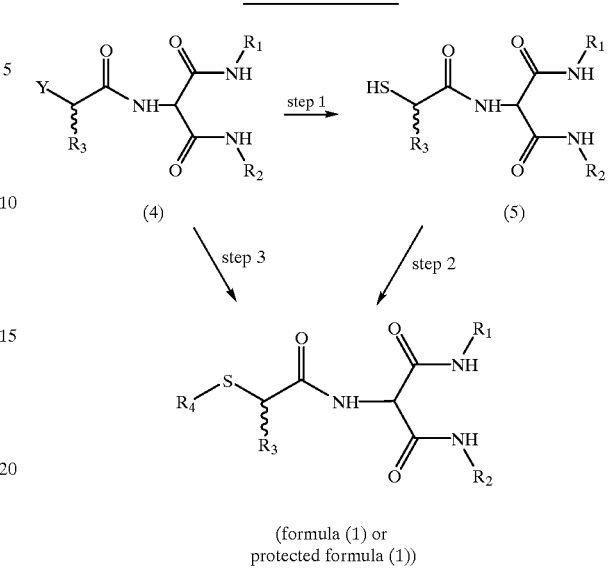

(formula (1) or protected formula (1))

In Reaction Scheme C, step 1, a compound of formula (4) in which Y is protected thio gives rise upon selective deprotection to give a compound of formula (5).

For example, compounds of formula (4) in which Y is a protected thio substituents are selectively deprotected to give a thiol of formula (5). Protected thio substituents include thioesters, such as thioacetyl or thiobenzoyl, thioethers, such as thiobenzyl, thio-4-methoxybenzyl, thiotriphenylmethyl, or thio-t-butyl, or unsymmetrical sulfides, such as dithioethyl or dithio-t-butyl. The use and selective removal of such thio protecting groups is well known and appreciated in the art and described in *Protective Groups in Organic Synthesis*, Theodora W. Greene (Wiley-Interscience, 2nd Edition, 1991).

In Reaction Scheme C, step 2, a compound of formula (5) undergoes modification reaction to give a compound of formula (1). Such modification reactions include, thiol esterification and disulfide formation.

Compounds of formula (1) in which $R_4$ is —C(O)$R_{10}$ or —C(O)—(CH$_2$)$_q$—X group can be synthesized by thiol esterifications according to techniques well known and appreciated by one of ordinary skill in the art, such as those disclosed in U.S. Pat. No. 5,424,425, issued Jun. 13, 1995.

For example, in a thiol esterification a compound of formula (5) is contacted with about an equimolar amount of an appropriate acid, such as HO—C(O)$R_{10}$ or HO—C(O)—(CH$_2$)$_q$—X in the presence of a suitable coupling agent to give a compound of formula (1) in which $R_4$ is —C(O)$R_{10}$ or —C(O)—(CH$_2$)$_q$—X. The reaction is carried out in the presence of a coupling agent such as 2-fluoro-1-methylpyridinium p-toluenesulfate, EDC (1-(3-dimethylaminopropyl)-3-ethylcarbodiimide hydrochloride), carbonyldiimidazole, EEDQ (1-ethoxycarbonyl-2-ethoxy-1,2-dihydroquinoline, DCC, or diethylcyanophosphonate in a suitable aprotic solvent such as methylene chloride. The reaction is generally carried out at temperature of between −20° C. and the boiling point of the solvent. Generally, the reaction requires 1 to 24 hours. The product can be isolated and purified by techniques well known in the art, such as extraction, evaporation, trituration, lyophilization, chromatography, and recrystallization.

Compounds of formula (1) in which $R_4$ is —S—G group can be synthesized according to techniques well known and appreciated by one of ordinary skill in the art, as disclosed in PCT Application No. WO 95/21839, published Aug. 17, 1995 and U.S. Pat. No. 5,491,143, issued Feb. 13, 1996, and U.S. Pat. No. 5,731,306, issued Mar. 24, 1998, and Roques, B. P. et al., *J. Med. Chem.* 33, 2473–2481 (1992).

For example, in a disulfide formation a compound of formula (5) is contacted with an appropriate compound of formula (7).

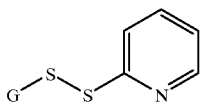

(7)

An appropriate compound of formula (7) is one which gives G as desired in the final product of formula (1) or gives rise upon deprotection to G as is desired in the final product of formula (1). In addition, the compound of formula (7) may have stereochemistry as desired in the final product of formula (1). The reaction is carried out in a suitable solvent, such as ethanol, methanol, dichloromethane, or mixtures of ethanol or methanol and dichloromethane. The solvent is degassed by passing a stream of nitrogen gas through it for 15 minutes before the reaction is carried out. The reaction is carried out using from 1.0 to 4.0 molar equivalents of an appropriate compound of formula (7). The reaction is carried out at temperatures of from 0° C. to the refluxing temperature of the solvent, with a temperature of 10° C. to 30° C. being preferred. The reaction generally requires from 1 to 48 hours. The product can be isolated by techniques well known in the art, such as extraction, evaporation, and precipitation and can be purified by chromatography and recrystallization.

In Reaction Scheme C, step 3, a compound of formula (4) in which Y is hydroxy or bromo can be displaced by an appropriate thiol, $HSR_4$, to give a compound of formula (1) or a protected compound of formula (1). In Reaction Scheme C, step 3, an appropriate thiol $HSR_4$ is one which gives $R_4$ as desired in the final product of formula (1) or gives rise upon deprotection to $R_4$ as desired in the final product of formula (1).

In Reaction Scheme C, step 3, a compound of formula (4) in which Y is hydroxy (obtained from protected hydroxy compounds of formula (4)) undergoes a displacement reaction with an appropriate thio introducing reagent by the method of Mitsunobu to give a compound of formula (4) in which Y is a protected thio substituent or —$SR_4$ as desired in the final compound of formula (1). For example, a compound of formula (4) in which Y is hydroxy reacts with thioacetic acid or thiobenzoic acid, triphenylphosphine, and diethylazodicarboxylate in a suitable aprotic solvent, such as tetrahydrofuran to give a compound of formula (4) in which Y is thioacetyl or thiobenzoyl. Selective removal of the thioacetic acid or thiobenzoic acid moiety gives the desired compound of formula (5). The product can be isolated and purified by techniques well known in the art, such as extraction, evaporation, trituration, lyophilization, chromatography, and recrystallization.

Also, in Reaction Scheme C, step 3, a compound of formula (4) in which Y is bromo undergo a displacement reaction with an appropriate thio introducing reagent to give a compound of formula (4) in which Y is protected thio substituent which gives rise upon deprotection and subsequent elaboration, if desired, the —$SR_4$ as desired in the final compound of formula (1). An appropriate thio introducing reagent is also one which introduces a group —$SR_4$ as desired in the final compound of formula (1).

For example, a solution of p-methoxybenzylmercaptan in a suitable organic solvent such as dimethylformamide is degassed and treated with a suitable base such as sodium hydride, sodium hydroxide, or cesium carbonate. After about 1 to 2 hours, a solution of a compound of formula (4) in which Y is bromo is added. The reaction may benefit from the addition of a suitable catalyst, such as tetra-n-butylammonium iodide. The reaction mixture is carried out for 1 to 25 hours at temperatures ranging form 0° C. to about 100° C. Selective removal of the 4-methoxybenzyl moiety gives the desired compound of formula (1). The product can be isolated and purified by techniques well known in the art, such as extraction, evaporation, trituration, lyophilization, chromatography, and recrystallization.

In addition, in Reaction Scheme C, step 3, a compound of formula (4) in which Y is bromo can be displaced by an appropriate thio ester, $Ph_3S$—$C(O)$—$(CH_2)_q$—X by techniques well known and appreciated in the art, as disclosed in U.S. Pat. No. 5,424,425, issued Jun. 13, 1995.

In Reaction Scheme C, in an optional step, a protected compound of formula (1) is deprotected to give a compound of formula (1). Such deprotection reactions are well known appreciated in the art and may include selective deprotections.

In Reaction Scheme D a compound of formula (4a) in which $R_{3'}$ gives rise to $R_{3''}$ and Y is —$SR_4$ as is desired in the final product of formula (1) or a protected thio substituent gives a compound of formula (1).

Reaction Scheme D

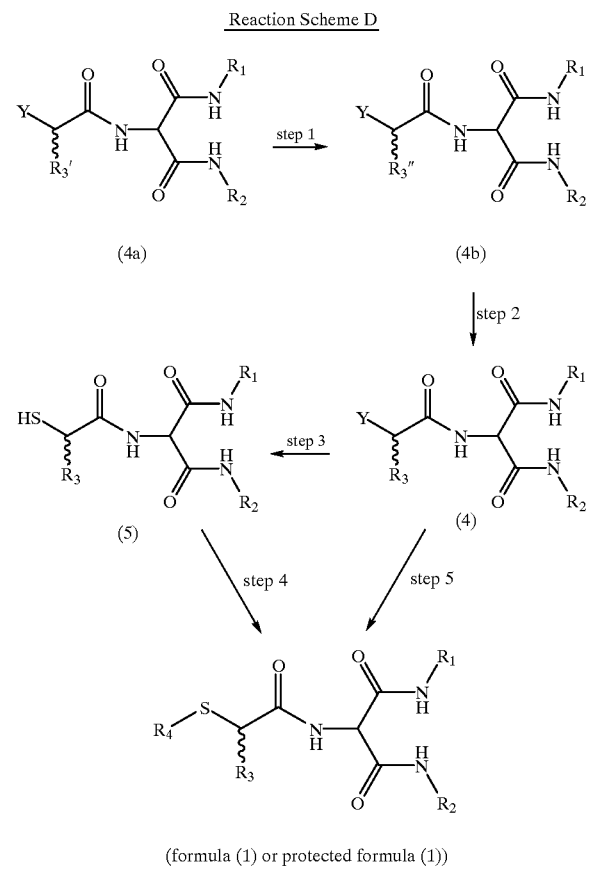

(formula (1) or protected formula (1))

In Reaction Scheme D, step 1, an appropriate compound of formula (4a) is deprotected, hydrolyzed, or reduced to give a compound of formula (4b). In Reaction Scheme D, step 1, an appropriate compound of formula (4a) is one in which $R_{3'}$ gives rise to a compound of formula (4b) in which $R_{3''}$ is $R_3$ as desired in the final product of formula (1) or $R_{3''}$ undergoes further derivitization (step 2) to give a compound of formula (4a) in which $R_3$ is a desired in the final product of formula (1). In Reaction Scheme D, step 1, an appropriate compound of formula (4a) is one in which Y is —$SR_4$ as desired in the final compound of formula (1) or Y is protected thio which gives rise upon deprotection or deprotection and further functionalization to give —$SR_4$, as desired, in the final product of formula (1) as described in Reactin Scheme C, step 2, above.

For example, in a deprotection a compound of formula (4a) in which $R_{3'}$ is —$(CH_2)_m$—W (phthalimido group) is contacted with a molar excess of hydrazine monohydrate to give a compound of formula (4b) in which $R_{3''}$ is —$(CH_2)_m$—$NHR_8$ in which $R_8$ is hydrogen. The reaction is typically carried out in a protic organic solvent, such as methanol or ethanol. The reaction is generally carried out at room temperature for a period of time ranging from 5–24 hours. The product can be isolated by techniques well known in the art, such as extraction, evaporation, and precipitation and can be purified by chromatography and recrystallization.

Alternately, for example, in a deprotection a compound of formula (4a) in which $R_{3'}$ is —$(CH_2)_m$—$NR_8$-t-Boc is contacted with a molar excess of a suitable acid to give a compound of formula (4b) in which $R_{3''}$ is —$(CH_2)_m$—$NHR_8$. The reaction is typically carried out in a organic solvent, such as methanol, ethanol, ethyl acetate, diethyl ether, or dioxane. Suitable acids for this reaction are well known in the art, including hydrochloric acid, hydrobromic acid, trifluoroacetic acid, and methanesulfonic acid. The reaction is generally carried out at room temperature for a period of time ranging from 1–10 hours. The product can be isolated by techniques well known in the art, such as extraction, evaporation, and precipitation and can be purified by chromatography and recrystallization.

For example, in a hydrolysis a compound of formula (4a) in which $R_{3'}$ is —$(CH_2)_m$—$C(O)OPg_3$ and $Pg_3$ is methyl or ethyl is contacted with about 1 to 2 molar equivalents of lithium hydroxide, sodium hydroxide, or potassium hydroxide to give a compound of formula (4b) in which $R_{3''}$ is —$(CH_2)_m$—$CO_2H$. The reaction is carried out in a suitable solvent, such as methanol, ethanol methanol/water mixtures, ethanol/water mixtures, or tetrahydrofuran/water mixtures and generally requires 1 to 24 hours. The reaction is carried out at temperatures of from about 0° C. to the refluxing temperature of the solvent. The resulting acid is isolated and purified by techniques well known in the art, such as acidification, extraction, evaporation, and precipitation and can be purified by trituration, precipitation, chromatography, and recrystallization.

For example, in a reduction a compound of formula (4b) in which $R_{3'}$ is —$(CH_2)_{m-1}$—$CO_2Pg_3$ in which $Pg_3$ is methyl or ethyl is contacted with a suitable reducing agent, such as lithium borohydride, diisobutylaluminum hydride, 9-borabicyclo[3.3.1]nonane, preferably lithium borohydride to provide a compound of formula (4b) in which $R_{3''}$ is —$(CH_2)_{m-1}$—$CH_2OH$. The reaction is carried out in a suitable solvent, such as dichloromethane, tetrahydrofuran, or toluene, with tetrahydrofuran being preferred. The reaction is carried out at a temperature of from about –30° C. to about 50° C. and generally requires from 2 to 12 hours. The product can be isolated by quenching, extraction, evaporation, and precipitation and can be purified by trituration, chromatography, and recrystallization.

In Reaction Scheme D, step 2, a compound of formula (4b) undergoes a derivitization reaction to give a compound of formula (4) in which $R_3$ is as desired in the final product of formula (1). Such derivitization reactions include hydrolysis of esters and ester formations as are well known in the art, ether formation, amine alkylation, formation of amides, urea formation, carbamate formation, and formation of sulfonamide. In Reaction Scheme D, step 2, the compound of formula (4b) is one in which Y is a protected thio group, such as thioacetyl, thiobenzoyl, 4-methoxybenzyl thiol or t-butylthiol.

For example, in an ether formation a compound of formula (4b) in which $R_{3''}$ is —$(CH_2)_{m-1}$—$CH_2OH$ is contacted with 1 to 10 molar equivalents of a suitable alkylating agent to give a compound of formula (4) in which $R_3$ is —$(CH_2)_m$—Z—Q in which Z is —O—. A suitable alkylating agent is one which transfers Q or protected Q as desired in the final product of formula (1), such as benzyl bromide, benzyl chloride, substituted benzyl bromide, substituted benzyl chloride, ethyl bromoacetate, t-butyl bromoaceate, ethyl 3-chloropropionate, ethyl 3-bromopropionate, ethyl 5-bromovalerate, ethyl 4-bromobutyrate, 3-chloropropionamide, 2-bromoethylbenzene, substituted 2-bromoethylbenzene, 1-chloro-3-phenylpropane, 1-bromo-2-bromoethylbenzene, 1-chloro-3-phenylpropane, 1-bromo-4-phenylbutane, and the like, or nitrogen mustards, including 2-dimethylaminoethyl chloride, 2-diethylaminoethyl chloride, and 3-dimethylaminopropyl chloride. The reaction is carried out in a suitable solvent, such as diethyl ether, tetrahydrofuran, dimethylformamide, dimethyl sulfoxide, or acetonitrile and using a suitable base, such as sodium hydride, potassium hydride, potassium t-butoxide, and lithium diisopropylamide. The reaction is generally carried out at temperatures of –70° C. and room temperature and require from about 1–24 hours. The product can be isolated by techniques well known in the art, such as extraction, evaporation, and precipitation and can be purified by chromatography and recrystallization.

Alternately, as appreciated by those skilled in the art, an ether formation can also be carried out by a procedure similar to the one above using a compound of formula (4b) in which $R_{3''}$ is —$(CH_2)_{m-1}$—$CH_2OH$ in which the hydroxy group is first converted to a leaving group, such as chloro, bromo, or mesylate and a suitable alcohol which transfers Q or protected Q as desired in the final product of formula (1), such as benzyl alcohol, substituted benzyl alcohol, phenol, substituted phenol, and the like. The conversion of hydroxy to leaving groups, such as chloro, bromo, and mesylate are well known and appreciated in the art.

For example, in an amine alkylation a compound of formula (4b) in which $R_{3''}$ is —$(CH_2)_m$—$NHR_8$ is contacted with 1 to 10 molar equivalents of a suitable akylating agent to give a compound of formula (4) in which $R_3$ is —$(CH_2)_m$—Z—Q in which Z is —$NR_8$—. The reaction may be carried out after protection of the amine function of $R_{3''}$ in which $R_8$ is hydrogen by a suitable protecting group, such as benzyl or t-Boc. For an amine alkylation a suitable alkylating agent is one as described above for the ether formation and also includes alkylhalides, such as methyl iodide, methyl bromide, ethyl bromide, propyl bromide, propyl chloride, butyl bromide, butyl chloride, and the like. The reaction is carried out in a suitable solvent, such as methanol, ethanol, dimethylformamide, or pyridine and using a suitable base, such as sodium carbonate, triethylamine, N,N-diisopropylethylamine or pyridine. The reaction is generally carried out at temperatures of room temperature to the refluxing temperature of the solvent and require from about 1–24 hours. The product can be isolated by techniques well known in the art, such as extraction, evaporation, and precipitation and can be purified by chromatography and recrystallization.

Alternately, for example, in an amine alkylation a compound of formula (4b) in which $R_{3''}$ is —$(CH_2)_m$—$NHR_8$ is contacted in a reductive alkylation with a suitable aldehyde to give a compound of formula (4) in which $R_3$ is —$(CH_2)_m$—Z—Q in which Z is —$NR_8$—. A suitable aldehyde is one which transfers Q or protected Q as desired in the final product of formula (1), such as benzaldehyde and substituted benzaldehydes. The reaction is carried out in a suitable solvent, such as methanol, ethanol, tetrahydrofuran, or mixtures of methanol or ethanol and tetrahydrofuran. The reaction may be carried out in the presence of a drying agent, such as sodium sulfate or molecular sieves. The reaction is carried out in the presence of from 1.0 to 6.0 molar equivalents of a suitable reducing agent, such as, sodium borohydride or sodium cyanoborohydride with sodium cyanoborohydride being preferred. It may be advantageous to maintain the pH in the range of about 4 to 6. The reaction is generally carried out at temperatures of from 0° C. to the refluxing temperature of the solvent. Generally, the reactions require 1 to 72 hours. The product can be isolated by techniques well known in the art, such as extraction, evaporation, and precipitation and can be purified by chromatography and recrystallization.

For example, in an amido formation a compound of formula (4b) in which $R_{3''}$ is is —$(CH_2)_m$—$CO_2H$ is contacted with a suitable amine in an amide formation to give a compound of formula (4) in which $R_3$ is —$(CH_2)_m$—Z—Q in which Z is amido. Such amide formation reactions using carboxy activation or suitable coupling agents are well known in the art and described above. A suitable amine, $HNR_8Q$, gives rise to $R_8$ and Q as desired in the final product of formula (1), such as methylamine, ethylamine, propylamine, butylamine, N-methyl benzylamine, benzyl β-alanine, 4-(3-aminopropyl)morpholine, and the like.

For example, in an amide formation a compound of formula (4b) in which $R_{3''}$ is is —$(CH_2)_m$—$NHR_8$ is contacted with a suitable carboxylic acid in an amide formation to give a compound of formula (4) in which $R_3$ is —$(CH_2)_m$—Z—Q in which Z is amide. Such amide formation reactions using carboxy activation or suitable coupling agents are well known in the art and described above. Suitable carboxylic acids, QC(O)—OH, are ones give rise to Q as desired in the final product of formula (1), such as benzoic acid, substituted benzoic acids, phenyl acetic acids, substituted phenylacetic acids, mono-t-butyl malonate, and the like.

For example, in a urea formation a compound of formula (4b) in which $R_{3''}$ is is —$(CH_2)_m$—$NHR_8$ is contacted with an appropriate isocyanate, O=C=N—Q, to give a compound of formula (4) in which $R_3$ is —$(CH_2)_m$—Z—Q in which Z is urea. An appropriate isocyanate is one which gives rise to Q as desired in the final product, such as phenyl isocyanate, substituted phenyl isocyanate, napthyl isocyanate, ethyl isocyanatoacetate, and the like. The reaction is carried out by adding an equivalent of, or a slight molar excess of, an appropriate isocyanate is added to a solution of a compound of formula (4b) in which $R_{3''}$ is —$(CH_2)_m$—$NHR_8$ in a suitable solvent, such as diethyl ether, benzene, or toluene. The reaction is carried out at temperature of from about 0° C. to the refluxing temperature of the solvent and require about 1–24 hours. The product can be isolated and purified by techniques well known in the art, such as filtration, extraction, evaporation, trituration, chromatography, and recrystallization.

For example, in an N-carbamoyl formation a compound of formula (4b) in which $R_{3''}$ is —$(CH_2)_m$—$NHR_8$ is contacted with an appropriate chloroformate to give a compound of formula (4) in which $R_3$ is —$(CH_2)_m$—Z—Q in which Z is N-carbamoyl. An appropriate chloroformate is one which gives rise to Q as desired in the final product of formula (1). Examples of chloroformates include benzyl chloroformate, naphthyl chloroformate, phenyl chloroformate, and substituted phenyl chloroformates, such as 4-chlorophenyl chloroformate, 4-methylphenyl chloroformate, 4-bromophenyl chloroformate, 4-fluorophenyl chloroformate, 4-methoxyphenyl chloroformate and the like. The reaction is carried out by adding an equivalent of, or a slight molar excess of, an appropriate chloro formate to a solution of a compound of formula (4b) in which $R_{3''}$ is —$(CH_2)_m$—$NHR_8$ in a suitable solvent, such as toluene, tetrahydrofuran, dimethylformamide, dichloromethane, pyridine, or chloroform. The reaction is carried out in the presence of an excess of a suitable base, such as triethylamine, sodium carbonate, potassium bicarbonate, pyridine or N,N-diisopropylethylamine. The reaction is carried out at a temperature of from −70° C. to the refluxing temperature of the solvent and generally requires from 30 minutes to 24 hours. The product can be isolated and purified by techniques well known in the art, such as extraction, evaporation, chromatography, and recrystallization.

For example, in an O-carbamoyl formation a compound of formula (4b) in which $R_{3''}$ is —$(CH_2)_{m-1}$—$CH_2OH$ is contacted with an appropriate isocyanate, as defined above for urea formation, to give a compound of formula (4) in which $R_3$ is —$(CH_2)_m$—Z—Q in which Z is O-carbamoyl. The reaction is carried out in a suitable solvent, such as diethyl ether, tetrahydrofuran, dimethylformamide, or acetonitrile. The reaction may be facilitated by the use of catalytic amount of a suitable base, such as sodium hydride, potassium hydride, or potassium t-butoxide. The reaction is generally carried out at temperatures of from −20° C. to room temperature and require from about 1–24 hours. The product can be isolated by techniques well known in the art, such as extraction, evaporation, and precipitation and can be purified by chromatography and recrystallization.

For example, in a sulfonamide formation to prepare a compound in which $R_3$ is —$(CH_2)_m$—$SO_2NR_8$—$Y_1$, a compound of formula (4b) in which $R_{3''}$ is —$(CH_2)_m$—$NHR_8$ is contacted with an appropriate sulfonamide forming reagent. An appropriate sulfonamide forming reagent, such as a sulfonyl chloride, $Y_1S(O)_2Cl$, or sulfonyl anhydride, $Y_1(O)_2S$—O—$S(O)_2$ $Y_1$, is one which gives rise to $Y_1$ as desired in the final product. Examples of appropriate sulfonamide forming reagents are, benzenesulfonyl chloride, 1-napthalenesulfonyl chloride, 2-napthalenesulfonyl chloride, dansyl chloride, N-morpholinylsulfonyl chloride, N-piperidinylsulfonyl chloride, 2,4,5-trichlorobenzenesulfonyl chloride, 2,5-dichlorobenzenesulfonyl chloride, 2,4,6-triisopropylbenzenesulfonyl chloride, 2-mesitylenesulfonyl chloride, 4-bromobenzenesulfonyl chloride, 4-fluorobenzenesulfonyl chloride, 4-chlorobenzenesulfonyl chloride, 4-methoxybenzenesulfonyl chloride, 4-t-butylbenzenesulfonyl chloride, p-toluenesulfonyl chloride, 2,3,4-trichlorobenzenesulfonyl chloride, 2,5-dimethoxybenzenesulfonyl chloride, 4-ethylbenzenesulfonyl chloride, 3,4-dimethoxybenzenesulfonyl chloride, 2,6-dichlorobenzenesulfonyl chloride, 3-bromobenzenesulfonyl chloride, 4-n-butylbenzenesulfonyl chloride, benzenesulfonic anhydride, 4-toluenesulfonic anhydride, and 2-mesitylenesulfonic anhydride. The reaction is carried out in a suitable solvent, such as tetrahydrofuran, dichloromethane, pyridine, or chloroform and in the presence of an excess of a suitable base, such as triethylamine, sodium carbonate, pyridine, or N,N-diisopropylethylamine. The reaction is carried out at a temperature of from −50° C. to the refluxing temperature of the solvent. The reaction generally requires from 30 minutes to 24 hours. The product can be isolated and purified by techniques well known in the art, such as extraction, evaporation, chromatography, and recrystallization.

In Reaction Scheme D, step 3, a compound of formula (4) in which $R_3$ is as desired in the final product of formula (1) undergoes a selective thiol deprotection to give a compound of formula (4). Such selective thiol deprotections using suitable protecting groups are well known and appreciated in the art as discussed in Reaction Scheme C, step 1, above.

In Reaction Scheme D, step 4, a compound of formula (4) undergoes a modification reaction to give a compound of formula (1) or protected compound of formula (1) as described in Reaction Scheme C, step 2, above.

In Reaction Scheme D, step 5, a compound of formula (4a) in which Y is protected thio is deprotected to give a compound of formula (1) or to a protected compound of formula (1).

In Reaction Scheme D, in an optional step, a protected compound of formula (1) is deprotected to give a compound of formula (1). Such deprotection reactions are well known appreciated in the art and may include selective deprotections.

Alternate routes for preparing the compounds of formula (3) in which Y is bromo are presented in Reaction Schemes F.1 and F.2.

Reaction Scheme F.1

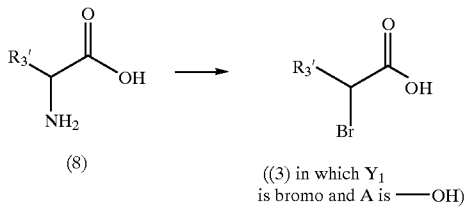

(8)

((3) in which $Y_1$ is bromo and A is ——OH)

In Reaction Scheme F.1, an appropriate α-amino carboxylic acid of formula (8) is deaminobrominated to give a compound of formula (3) in which Y is bromo and A is —OH. An appropriate α-amino carboxylic acid of formula (8), and protected forms thereof, is one which is one in which $R_{3'}$ is $R_3$ as desired in the final product of formula (1) or gives rise after deprotection to $R_3$ as desired in the final product of formula (1) In addition, α-amino carboxylic acid of formula (8) may also be one in which the stereochemistry at the $R_{3'}$ bearing carbon gives rise after displacement to the stereochemistry as desired at that carbon in the final product of formula (1). Such appropriate α-amino carboxylic acid of formula (8), are commercially available or may be readily prepared by techniques and procedures well known and appreciated by one of ordinary skill in the art. For example, L-alanine, D-alanine, L-valine, D-valine, D-norvaline, L-leucine, D-leucine, D-isoleucine, D-tert-leucine, glycine, L-glutamic acid, D-glutamic acid, L-glutamine, D-glutamine, L-lysine, D-lysine, L-ornithine, D-ornithine, (D)-(−)-2-aminobutyric acid, D-threonine, D-homoserine, D-allothreonine, D-serine, D-2-aminoadipic acid, D-aspartic acid, D-glutamic acid, D-lysine hydrate, 2,3-diaminopropionic acid monohydrobromide, D-ornithine hydrochloride, D,L-2,4-diaminobutyric acid dihydrochloride, L-meta-tyrosine, D-4-hydroxyphenylglycine, D-tyrosine, L-phenylalanine, D-phenylalanine, D,L-2-fluorophenylalanine, beta-methyl-D,L-phenylalanine hydrochloride, D,L-3-fluorophenylalanine, 4-bromo-D,L-phenylalanine, L-phenylalanine, L-phenylglycine, D-phenylglycine, D,L-4-fluorophenylalanine, 4-iodo-D-phenylalanine, D-homophenylalanine, D,L-2-fluorophenylglycine, D,L-4-chlorophenylalanine, and the like, are all commercially available and the methods in D. A. Evans, et al. *J. Am. Chem. Soc.,* 112, 4011–4030 (1990); S. Ikegami et al. *Tetrahedron,* 44, 5333–5342 (1988); W. Oppolzer et al. *Tet. Lets.* 30, 6009–6010 (1989); *Synthesis of Optically Active α-Amino-Acids,* R. M. Williams (Pergamon Press, Oxford 1989); M. J. O'Donnell ed.: *α-Amino-Acid Synthesis,* Tetrahedron Symposia in print, No. 33, *Tetrahedron* 44, No. 17 (1988); U. Schöllkopf, *PureAppl. Chem.* 55, 1799 (1983); U. Hengartner et al. *J. Org. Chem.,* 44, 3748–3752 (1979); M. J. O'Donnell et al. *Tet. Lets.,* 2641–2644 (1978); M. J. O'Donnell et al. *Tet. Lets.* 23, 4255–4258 (1982); M. J. O'Donnell et al. *J. Am. Chem. Soc.,* 110, 8520–8525 (1988).

The deaminobromination described in Reaction Scheme F.1 can be performed utilizing conditions described in Compagnone, R. S. and Rapoport, H., *J. Org. Chem.,* 51, 1713–1719 (1986); U.S. Pat. No. 5,322,942, issued Jun. 21, 1994; Overberger, C. G. and Cho, I., *J. Org. Chem.,* 33, 3321–3322 (1968); or Pfister, K. et al., *J. Am. Chem. Soc.,* 71, 1096–1100 (1949).

For example, an α-amino carboxylic acid of formula (8) and a suitable bromide, such as hydrogen bromide or potassium bromide in acidic solution, such as sulfuric acid, is treated with sodium nitrite. The reaction temperature is carried out a temperatures of from about −25° C. to about ambient temperature and require about 1 to 5 hours. The product can be isolated and purified by techniques well known in the art, such as acidification, extraction, evaporation, chromatography, and recrystallization to give the compound of formula (3) in which Y is bromo and A is —OH. The product can be isolated and purified by techniques well known and appreciated in the art, such as acidification, basification, filtration, extraction, evaporation, trituration, chromatography, and recrystallization.

Reaction Scheme F2

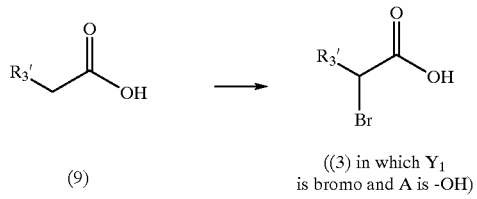

(9)

((3) in which $Y_1$ is bromo and A is -OH)

In Reaction Scheme F.2, an appropriate carboxylic acid of formula (9) is brominated to give compound of formula (3) in which Y is bromo and A is —OH. An appropriate carboxylic acid of formula (9), and protected forms thereof, is one which is one in which $R_{3'}$ is $R_3$ as desired in the final product of formula (1) or gives rise after deprotection to $R_3$ as desired in the final product of formula (1).

For example, a mixture of a carboxylic acid of formula (9) and dry red phosphorous are treated dropwise with bromine at temperature ranging from about −20° to about 10° C. The reaction mixture is then warmed to room temperature and then heated to about 80° C. for about 2–5 hours. The reaction mixture is then cooled to room temperature, poured into water containing sodium bisulfite, and neutralized using solid sodium carbonate. The aqueous layer is extracted and acidified with a suitable acid, such as concentrated hydrochloric acid. The precipitate is collected by filtration and dried to give the compound of formula (3) or formula (3b2)in which Y is bromo and A is —OH. The product can be isolated and purified by techniques well known and appreciated in the art, such as acidification, basification, filtration, extraction, evaporation, trituration, chromatography, and recrystallization.

Compounds of formula (8) and (9) in which $R_{3'}$ is a —$(CH_2)_m$—W for use in Reaction Schemes F.1 and F.2 are prepared according to Reaction Scheme G.1 and G.2.

Reaction Scheme G.1

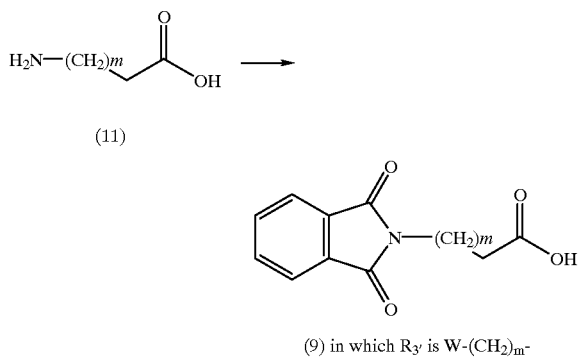

(9) in which $R_{3'}$ is W-$(CH_2)_m$-

In Reaction Scheme G.1 an appropriate ω-amino carboxylic acid of formula (11) is converted to an compound of formula (9) in which $R_{3'}$ is W—$(CH_2)_m$—. An appropriate ω-amino carboxylic acid of formula (11) is one in which m is as desired in the final product of formula (1) and are readily available in the art. For example, the reaction is carried out in a suitable polar solvent, such as water, ethanol, diethyl ether, tetrahydrofuran, or a water/ethereal solvent mixture using a suitable base, such as sodium carbonate and N-carbethoxyphthalimide. The reaction mixture is typically stirred at about ambient temperature for 1–5 hours. The product can be isolated and purified by techniques well known in the art, such as acidification, extraction, evaporation, chromatography, and recrystallization to give the desired compound of formula (9) in which $R_{3'}$ is W—$(CH_2)_m$—.

Reaction Scheme G.2

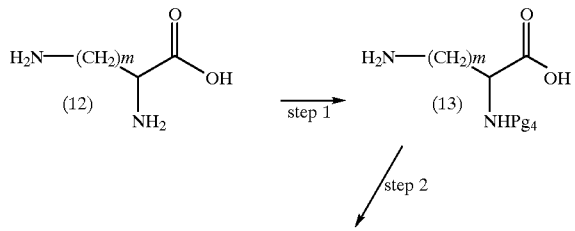

-continued

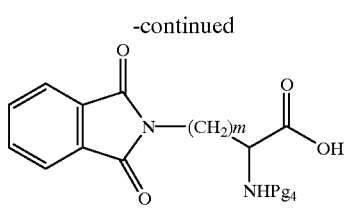

(14)

↓ step 3

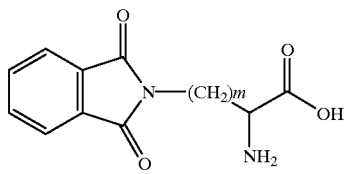

(8) in which $R_{3'}$ is W—$(CH_2)_{\overline{m}}$—

Reaction Scheme G.2, step 1, an appropriate α,ω-diamino acid of formula (12) undergoes a selective N-α-protection to give an N-α-protected-ω-diamino acid of formula (13). An appropriate α,ω-diamino acid of formula (12) is one in which m is as desired in the final product of formula (1).

For example, a selective N-α-protection of a suitable α,ω-diamino acid, such as L-lysine (formula 12 in which m is 4), is accomplished by masking the ω-amino group by formation of a benzylidene imine. The benzylidene imine is formed by dissolving L-lysine monohydrochloride in lithium hydroxide and cooling the solution to a temperature ranging from about 0° to 10° C. Freshly distilled benzaldehyde is then added and the solution is shaken. N-ω-benzylidene-L-lysine is recovered by filtration and evaporation. The α-amino group of the N-ω-benzylidene-L-lysine then undergoes protection, such as the introduction of a Cbz or t-Boc group, followed by hydrolytic cleavage of the imine in situ to give N-α-benzyloxy-carbonyl-L-lysine. Accordingly, N-ω-benzylidene-L-lysine is added to a mixture of sodium hydroxide and ethanol, cooled to a temperature of from about −5° to about −25° C. Then, precooled solutions of benzyloxycarbonyl chloride in a solvent, such as ethanol, is added to the reaction mixture. The temperature is maintained in a range of from about −10° to about −25° C. during the course of addition, and may allowed to rise afterwards. The reaction mixture is then acidified using a suitable acid, such as precooled hydrochloric acid, and N-α-benzyloxycarbonyl-L-lysine, which corresponds to formula (13) where m is 4, is recovered by filtration evaporate and recrystallization.

In Reaction Scheme G.2, step 2, N-α-benzyloxycarbonyl-L-lysine or other compounds of formula (13) is converted to ω-phthalimido-α-benzyloxycarbonyl-L-lysine or other ω-phthalimido-α-aminoprotected carboxylic acid of formula (14) by the method described in Reaction Scheme G.1, above.

In Reaction Scheme G.2, step 3, the ω-phthalimido-α-aminoprotected carboxylic acid of formula (14) is deprotected to give compound of formula (8) in which $R_{3'}$ is W—$(CH2)_m$—.

For example, ω-phthalimido-α-benzyloxycarbonyl-L-lysine is contacted with hydrogen in the presence of a hydrogenation catalyst, such as 10% palladium/carbon. The reactants are typically contacted in a suitable solvent mixture such as ethanol, methanol, water, ethanol/water mixtures, or methanol/water mixtures. The reactants are typically shaken under a hydrogen atmosphere of 35–45 psi at room temperature for a period of time ranging from 5–24 hours. The product is typically recovered by filtration and evaporation of the solvent.

A route for preparing the compounds of formula (3) and formula (3b2) in which $Y_1$ is protected thio is presented in Reaction Scheme H. The reagents and starting materials are readily available to one of ordinary skill in the art. In Reaction Scheme H all substituents, unless otherwise indicated, are as previously defined.

Reaction Scheme H

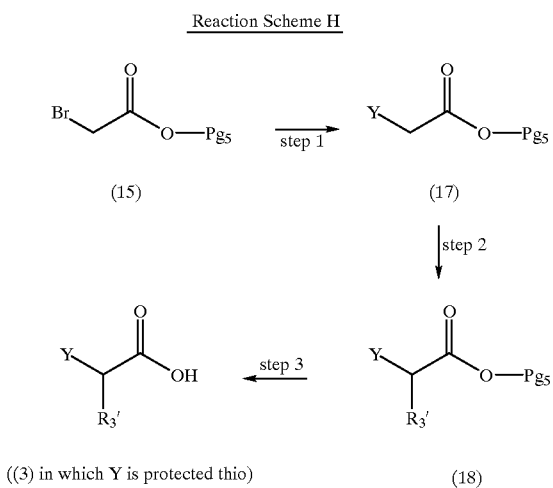

((3) in which Y is protected thio)

In Reaction Scheme H, step 1, a bromoacetate of formula (15) is contacted with an appropriate thiol to give a protected acetic acid ester of formula (17). In a bromoacetate of formula (15) $Pg_5$ is a protecting group, such as methyl, ethyl, t-butyl, and benzyl. An appropriate thiol is one which gives rise to a protected thio group, Y, in the product of formula (3b). In Reaction Scheme H, step 1, the use of 4-methoxybenzylmercaptan is preferred.

For example, a bromoacetate of formula (15) is contacted with an appropriate thiol in a suitable organic solvent, such as dimethylformamide. Advantageously, the solvent is degassed. The reaction is carried out using a suitable base, such as sodium hydroxide, triethylamine, or N,N-diisopropylethylamine. The reaction is carried out at temperatures of from about –50° to about ambient temperature and requires about 1 to 72 hours. The protected acetic acid ester of formula (17) can be isolated and purified by methods well known and appreciated in the art, such as extraction, evaporation, chromatography, and distillation, and recrystallization.

In Reaction Scheme H, step 2, the protected acetic acid ester of formula (17) is alkylated with an appropriate akylating agent to give a compound of formula (18). In Reaction Scheme H, step 2, an appropriate alkylating agent is one which transfers $R_3$, which is $R_3$ as desired in the final product of formula (1) or gives rise after deprotection to $R_3$ as desired in the final product of formula (1) or gives rise to $R_{3''}$ as defined in Reaction Scheme D, step 1. Appropriate alkylating agents include alkylhalides, such as methyl iodide, methyl bromide, ethyl bromide, propyl bromide, propyl chloride, butyl bromide, butyl chloride, and the like; benzyl bromide, benzyl chloride, substituted benzyl bromide, substituted benzyl chloride, ethyl bromoacetate, t-butyl bromoaceate, ethyl 3-chloropropionate, ethyl 3-bromopropionate, ethyl 5-bromovalerate, ethyl 4-bromobutyrate, 3-chloropropionamide, 2-bromoethylbenzene, substituted 2-bromoethylbenzene, 1-chloro-3-phenylpropane, 1-bromo-4-phenylbutane, and the like, N-(2-bromoethyl)phthalimide, , N-(3-bromopropyl)phthalimide, N-(4-bromobutyl)phthalimide, and the like; 1-bromo-2-phenylethane, 1-bromo-3-phenylpropane, 1-bromo-4-phenylbutane, and the like.

For example, a protected acetic acid ester of formula (17) is alkylated with an appropriate alkylating agent. The reaction is carried out in a suitable solvent, such as diethyl ether, tetrahydrofuran, dimethylformamide, and toluene using a suitable base, such as sodium hydride, potassium hydride, potassium t-butoxide, lithium bis(trimethylsilyl)amide, sodium bis(trimethylsilyl)amide, potassium bis(trimethylsilyl)amide, or lithium diisopropylamide. The reaction is generally carried out at temperatures of about –70° C. to about room temperature and require from about 1–24 hours. The product can be isolated by techniques well known in the art, such as extraction, evaporation, and precipitation and can be purified by chromatography and recrystallization.

In Reaction Scheme H, step 3, the compound of formula (18) the carboxy protecting group $Pg_5$ is selectively removed to give a compound of formula (3) in which Y is protected thio. Such deprotection of esters to acids in the presence of suitable thio protecting groups are well known and appreciated in the art.

The following examples and preparations present typical syntheses as described in the Reaction Schemes above. These examples and preparations are understood to be illustrative only and are not intended to limit the scope of the invention in any way.

Preparation 1.1

2-(t-Butoxycarbonylamino)malonic acid

Combine diethyl aminomalonate hydrochloride (5.0 g, 23.6 mmol), triethylamine (3.30 mL, 23.6 mmol), and dichloromethane (80 mL). Add di-t-butyl dicarbonate (5.4 g, 24.8 mmol). After 18 hours, extract with an aqueous 5% sulfuric acid solution, a saturated aqueous sodium bicarbonate solution, and then brine. Dry the organic layer over $Na_2SO_4$, filter, and evaporate in vacuo to give a residue. Chromatograph the residue on silica gel eluting with 3/2 hexane/ethyl acetate to give diethyl t-butoxycarbonylaminomalonate (87%).

Combine diethyl t-butoxycarbonylaminomalonate (4.55 g, 16.5 mmol), a 6 M aqueous sodium hydroxide solution (6.65 mL, 40 mmol), and ethanol (30 mL). After 18 hours, evaporate in vacuo to remove most of the ethanol, dilute with water (50 mL) and extract with diethyl ether. Acidify to a pH of about 3 with aqueous 12M hydrochloric acid and extract twice with ethyl acetate. Dry the combined organic layers over $Na_2SO_4$, filter, and concentrate in vacuo to give the title compound (61%).

Preparation 1.2

2-(t-Butoxycarbonylamino)malonic acid

Combine diethyl aminomalonate hydrochloride (13.34 g, 63.0 mmol), triethylamine (8.8 mL, 63.0 mmol), and dichloromethane (220 mL). Add di-t-butyl dicarbonate (14.4 g, 66.2 mmol). After 18 hours, extract with an aqueous 5% sulfuric acid solution, a saturated aqueous sodium bicarbonate solution, and brine. Dry the organic layer over $Na_2SO_4$, filter, and evaporate in vacuo to give diethyl t-butoxycarbonylaminomalonate (103%).

Combine diethyl t-butoxycarbonylaminomalonate (22.72 g, 82.5 mmol), a 6 M aqueous sodium hydroxide solution (55 mL, 330 mmol), and ethanol (150 mL). After 56 hours, evaporate in vacuo to remove most of the ethanol, dilute with water (40 mL). Cool and acidify to a pH of about 3 with concentrated hydrochloric acid. Freeze dry to give the title compound and sodium chloride as a powder.

Preparation 2

2-(R)-2-Bromo-3-methylbutyric acid

Combine D-valine (4.7 g, 40.0 mmol) and an aqueous 2.5 M sulfuric acid solution. Cool to about −5° C. Add aqueous hydrobromic acid (13.2 g, 48%, 40 mmol). Add a solution of sodium nitrite (2.8 g, 40 mmol) in water (20 mL). After 2 hours, warm to about 5° C. After 18 hours, extract three times with ethyl acetate. Dry the combined organic layers over Na$_2$SO$_4$, filter, and evaporate in vacuo to give a residue. Chromatograph the residue on silica gel eluting with 1/1/0.1 dichloromethane/ethyl acetate/acetic acid to give a residue. Rechromatograph the residue on silica gel eluting with 1/1/0.5 dichloromethane/ethyl acetate/acetic acid to give the title compound (35%).

EXAMPLE 1

N,N'-Diphenethyl-2-((S)-2-mercapto-3-methylbutyrylamino)malonamide

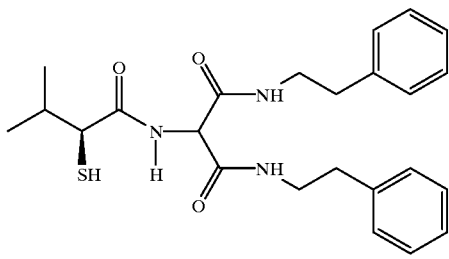

1.1 Synthesis of N,N'-diphenethyl-2-(t-butoxycarbonylamino)malonamide

Combine t-butoxycarbonylaminomalonic acid (0.465 g, 2.12 mmol), phenethylamine (0.715 mL, 5.70 mmol), and dichloromethane (25 mL). Add N-methylmorpholine (0.752 mL, 6.85 mmol). Cool in an ice bath. Add benzotriazol-1-yloxy-tris(pyrrolidino)phosphonium hexafluorophosphate complex (3.15 g, 6.85 mmol). Remove the ice bath and allow to warm to ambient temperature. After 18 hours, dilute the reaction mixture with ethyl acetate, extract with an aqueous 5% sulfuric acid solution, a saturated sodium bicarbonate solution, and then brine. Dry the organic layers over Na$_2$SO$_4$, filter, and evaporate in vacuo to give a residue. Chromatograph the residue on silica gel eluting with 2/1 ethyl acetate/hexane to give the title compound.

1.2 Synthesis of N,N'-diphenethyl-2-aminomalonamide trifluoroacetic acid salt

Combine N,N'-diphenethyl-2-(t-butoxycarbonylamino)malonamide (0.571 g, 1.35 mmol) and dichloromethane (10 mL). Add trifluoroacetic acid (1.8 mL). After 2.5 hours, evaporate in vacuo to give a residue. Add hexanes and carbon tetrachloride to co-evaporate residual trifluoroacetic acid and evaporate in vacuo to give the title compound (100%).

1.3 Synthesis of N,N'-Diphenethyl-2-((R)-2-bromo-3-methylbutyrylamino)malonamide Combine N,N'-diphenethyl-2-aminomalonamide trifluoroacetic acid salt (0.285 g, 0.655 mmol) and dichloromethane (5 mL). Add (R)-2-bromo-3-methylbutyric acid (0.118 g, 0.655 mmol), N-methylmorpholine (0.10 mL, 0.983 mmol), and 1-ethyl-3-(3-(dimethylamino)propyl) carbodiimide hydrochloric acid salt (0.14 g, 0.725 mmol), and 1-hydroxybenztriazole hydrate (0.10 g, 0.72 mmol). After 18 hours, evaporate the reaction mixture in vacuo, dilute the concentrated reaction mixture with ethyl acetate, extract with an aqueous 5% sulfuric acid solution, a saturated sodium bicarbonate solution, and then brine. Saturate each of the aqueous layers with sodium chloride and extract four times with ethyl acetate. Combine the organic layers, dry over Na$_2$SO$_4$, filter, and evaporate in vacuo to give a residue. Chromatograph the residue on silica gel eluting with 1/1 ethyl acetate/hexane to give the title compound (67%).

1.4 Synthesis of N,N'-diphenethyl-2-((S)-2-thioacetyl-3-methylbutyrylamino)malonamide Combine N,N'-diphenethyl-2-((R)-2-bromo-3-methylbutyrylamino)malonamide (0.20 g, 0.41 mmol), thioacetic acid (0.08 mL, 1.1 mmol), and dimethylformamide (8 mL). Degas by repeated cycles of vacuum and filling with nitrogen gas. Add cesium carbonate (0.215 g, 0.664 mmol). After 18 hours, dilute with water and extract with ethyl acetate. Extract the organic layer with brine, dry over Na$_2$SO$_4$, filter, and evaporate in vacuo to give a residue. Chromatograph the residue on silica gel eluting with 1/1 hexane ethyl acetate to give the title compound.

1.5 Synthesis of N,N'-diphenethyl-2-((S)-2-mercapto-3-methylbutyrylamino)malonamide Cool methanol (10 mL) in an ice bath and bubble with ammonia gas for about 15 minutes. Add a cooled (about 0° C.) solution of N,N'-diphenethyl-2-((S)-2-thioacetyl-3-methylbutyrylamino)malonamide (0.17 g, 0.35 mmol) in degassed methanol (10 mL). After 1 hour, evaporate in vacuo to give a residue. Chromatograph the residue on silica gel eluting sequentially with 3/2 hexane ethyl acetate and then 1/1 hexane ethyl acetate give the title compound (89%).

EXAMPLE 2

N,N'-Diphenethyl-2-((S)-2-mercapto-3-phenylpropionylamino)malonamide

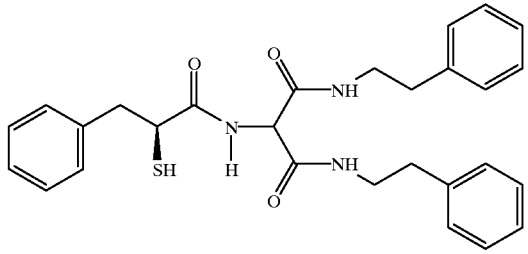

2.1 Synthesis of N,N'-Diphenethyl-2-((R)-2-bromo-3-phenylpropionylamino)malonamide Prepare by the method of Example 1.3 using N,N'-diphenethyl-2-aminomalonamide trifluoroacetic acid salt (0.61 g, 0.600 mmol), (R)-2-bromo-3-phenylpropionic acid (0.137 g, 0.600 mmol), N-methylmorpholine (0.20 mL, 1.8 mmol), 1-ethyl-3-(3-(dimethylamino)propyl)carbodiimide hydrochloric acid salt (0.14 g, 0.72 mmol), and 1-hydroxybenztriazole hydrate (0.097 g, 0.72 mmol) in dichloromethane (10 mL). Purify by chromatography on silica gel eluting with 1/1 ethyl acetate/hexane to give the title compound (60%).

2.2 Synthesis of N,N'-diphenethyl-2-((S)-2-thioacetyl-3-phenylpropionylamino)malonamide Prepare by the method of Example 1.4 using N,N'-diphenethyl-2-((R)-2-bromo-3-phenylpropionylamino) malonamide (0.11 g, 0.21 mmol), thioacetic acid (0.05 mL, 0.62 mmol), and cesium carbonate (0.10 g, 0.31 mmol) in dimethylformamide (8 mL). Purify by chromatography on silica gel eluting with 1/1 hexane ethyl acetate to give the title compound (92%).

2.3 Synthesis of N,N'-diphenethyl-2-((S)-2-mercapto-3-phenylpropionylamino)malonamide Prepare by the method of Example 1.5 using N,N'-diphenethyl-2-((S)-2-thioacetyl-3-phenylpropionylamino) malonamide (0.10 g, 0.192 mmol). Purify by chromatography on silica gel eluting with 1/1 hexane ethyl acetate give the title compound (83%).

Preparation 3

2-(S)-2-Thioacetyl-4-pheynylbutyric acid

Combine D-homophenylalanine (5.0 g, 28.0 mmol) and an aqueous 2.5 M sulfuric acid solution (28 mL). Cool to about −5° C. Add aqueous hydrobromic acid (6.35 mL, 48%, 56 mmol). Add a solution of sodium nitrite (1.95 g, 28 mmol) in water (15 mL) over about 30 minutes. After 2 hours, warm to about 0° C. After 18 hours, extract three times with ethyl acetate. Dry the combined organic layers over Na$_2$SO$_4$, filter, and evaporate in vacuo to give a residue. Chromatograph the residue on silica gel eluting with 9/1/0.5 dichloromethane/ethyl acetate/acetic acid to give 2-(R)-2-bromo-4-pheynylbutyric acid (54%).

Combine 2-(R)-2-bromo-4-pheynylbutyric acid (0.486 g, 2.05 mmol), thioacetic acid (0.40 mL, 5.5 mmol), and dimethylformamide (40 mL). Degas by repeated cycles of vacuum and filling with nitrogen gas. Add cesium carbonate (1.08 g, 0.32 mmol). After 18 hours, dilute with water and extract with ethyl acetate. Extract the organic layer with brine, dry over Na$_2$SO$_4$, filter, and evaporate in vacuo to give the title compound.

EXAMPLE 3

N,N'-Diphenethyl-2-((S)-2-mercapto-4-phenylbutyrylamino)malonamide

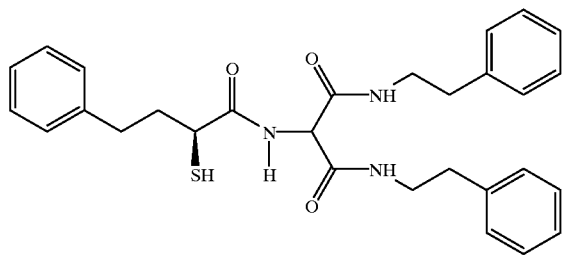

3.1 Synthesis of N,N'-diphenethyl-2-(t-butoxycarbonylamino)malonamide

Combine a mixture of t-butoxycarbonylaminomalonic acid and sodium chloride from Preparation 1.2 (5.0 g, 13.7 mmol), phenethylamine (4.32 mL, 34.3 mmol), and tetrahydrofuran (25 mL). Cool in an ice bath. Remove the ice bath. Add N-methylmorpholine (3.8 mL, 34.3 mmol), 1-ethyl-3-(3-(dimethylamino)propyl)carbodiimide hydrochloric acid salt (6.58 g, 34.3 mmol), and 1-hydroxybenztriazole hydrate (4.63 g, 34.3 mmol). Allow to warm to ambient temperature. After 18 hours, dilute the reaction mixture with ethyl acetate, extract with an aqueous 5% sulfuric acid solution, a saturated sodium bicarbonate solution, and then brine. Dry the organic layers over Na$_2$SO$_4$, filter, and evaporate in vacuo to give a residue. Chromatograph the residue on silica gel eluting with 2/1 ethyl acetate/hexane to give the title compound (84%).

3.2 Synthesis of N,N'-diphenethyl-2-aminomalonamide trifluoroacetic acid salt Combine N,N'-diphenethyl-2-(t-butoxycarbonylamino) malonamide (0.425 g, 1.00 mmol) and dichloromethane (7 mL). Add trifluoroacetic acid (1.5 mL). After 2.5 hours, evaporate in vacuo to give a residue. Repeatedly, add carbon tetrachloride to co-evaporate residual trifluoroacetic acid and evaporate in vacuo to give the title compound.

3.3 Synthesis of N,N'-diphenethyl-2-((S)-2-thioacetyl-4-phenylbutyrylamino)malonamide Combine N,N'-diphenethyl-2-aminomalonamide trifluoroacetic acid salt (0.50 g, 1.0 mmol) and dichloromethane (15 mL). Add (R)-2-thioacetyl-4-phenylbutyric acid (0.545 g, 1.0 mmol), N-methylmorpholine (0.22 mL, 2.0 mmol), and 1-ethyl-3-(3-(dimethylamino)propyl)carbodiimide hydrochloric acid salt (0.23 g, 1.2 mmol), and 1-hydroxybenztriazole hydrate (0.16 g, 1.2 mmol). After 18 hours, evaporate the reaction mixture in vacuo, dilute the concentrated reaction mixture with ethyl acetate, extract with an aqueous 5% sulfuric acid solution, a saturated sodium bicarbonate solution, and then brine. Extract each aqueous layer with ethyl acetate. Combine the organic layers, dry over Na$_2$SO$_4$, filter, and evaporate in vacuo to give a residue. Chromatograph the residue on silica gel eluting with 3/2 ethyl acetate/hexane to give the title compound (92%).

3.4 Synthesis of N,N'-diphenethyl-2-((S)-2-mercapto-4-phenylbutyrylamino)malonamide Cool methanol (15 mL) in an ice bath and bubble with ammonia gas for about 15 minutes. Add a cooled (about 0°

C.) solution of N,N'-diphenethyl-2-((S)-2-thioacetyl-4-phenylbutyrylamino)malonamide (0.50 g, 0.92 mmol) in degassed methanol (15 mL). After 1 hour, evaporate in vacuo to give a residue. Chromatograph the residue on silica gel eluting with 3/2 hexane ethyl acetate to give the title compound (28%).

EXAMPLE 4

N,N'-Dibenzyl-2-((S)-2-mercapto-3-phenylpropionylamino)malonamide

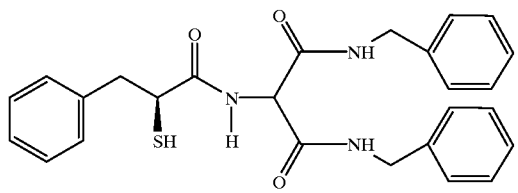

4.1 Synthesis of N,N'-dibenzyl-2-(t-butoxycarbonylamino)malonamide

Combine t-butoxycarbonylaminomalonic acid (0.438 g, 2.00 mmol), benzylamine (0.436 mL, 4.0 mmol), and dichloromethane (10 mL). Add N-methylmorpholine (0.55 mL, 5.00 mmol) ), 1-ethyl-3-(3-(dimethylamino)propyl) carbodiimide hydrochloric acid salt (0.96 g, 5.0 mmol), and 1-hydroxybenztriazole hydrate (0.67 g, 5.0 mmol). After 18 hours, concentrate in vacuo, dilute the concentrated reaction mixture with ethyl acetate, extract with an aqueous 5% sulfuric acid solution, a saturated sodium bicarbonate solution, and then brine. Dry the organic layer over $Na_2SO_4$, filter, and evaporate in vacuo to give a residue. Chromatograph the residue on silica gel eluting with 3/2 ethyl acetate/hexane to give the title compound (52%).

4.2 Synthesis of N,N'-dibenzyl-2-aminomalonamide trifluoroacetic acid salt

Combine N,N'-dibenzyl-2-(t-butoxycarbonylamino) malonamide (0.415 g, 1.04 mmol) and dichloromethane (7 mL). Add trifluoroacetic acid (1.0 mL). After 2.5 hours, evaporate in vacuo dry under high vacuum to give the title compound.

4.3 Synthesis of N,N'-dibenzyl-2-((R)-2-bromo-3-phenylpropionylamino)malonamide Combine N,N'-dibenzyl-2-aminomalonamide trifluoroacetic acid salt (0.41 g, 1.04 mmol), (R)-2-bromo-3-phenylpropionic acid (0.262 g, 1.15 mmol), N-methylmorpholine (0.23 mL, 2.08 mmol), 1-ethyl-3-(3-(dimethylamino)propyl)carbodiimide hydrochloric acid salt (0.22 g, 1.15 mmol), and 1 -hydroxybenztriazole hydrate (0.155 g, 1.15 mmol) in dichloromethane (5 mL). After 18 hours, extract with an aqueous 5% sulfuric acid solution, a saturated sodium bicarbonate solution, and then brine. Dry the organic layer over $Na_2SO_4$, filter, and evaporate in vacuo to give a residue. Chromatograph the residue on silica gel eluting with 1/1 ethyl acetate/hexane to give the title compound.

4.4 Synthesis of N,N'-dibenzyl-2-((S)-2-thioacetyl-3-phenylpropionylamino)malonamide Combine N,N'-dibenzyl-2-((R)-2-bromo-3-phenylpropionylamino)malonamide (0.49 g, 0.97 mmol) and thioacetic acid (0.172 mL, 2.42 mmol) in dimethylformamide (15 mL). Degas by repeated cycles of vacuum and filing with nitrogen. Add cesium carbonate (0.473 g, 1.45 mmol). After 18 hours, dilute the reaction mixture with water and extract twice with ethyl acetate. Combine the organic layers, extract with brine, dry over $Na_2SO_4$, filter, and evaporate in vacuo to give a residue. Chromatograph the residue on silica gel eluting with 3/2 ethyl acetate/hexane to give the title compound (46%).

4.5 Synthesis of N,N'-dibenzyl-2-((S)-2-mercapto-3-phenylpropionylamino)malonamide Cool methanol (12 mL) in an ice bath and bubble with ammonia gas for about 15 minutes. Add a cooled (about 0° C.) solution of N,N'-dibenzyl-2-((S)-2-thioacetyl-3-phenylpropionylamino)malonamide (0.224 g, 0.445 mmol) in degassed methanol (12 mL). After 1 hour, evaporate in vacuo to give a residue. Chromatograph the residue on silica gel eluting with 3/2 ethyl acetate/hexane give the title compound.

EXAMPLE 5

N,N'-Di-(3-phenylpropyl)-2-((S)-2-mercapto-3-phenylpropionylamino)malonamide

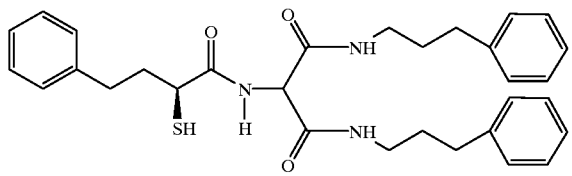

5.1 Synthesis of N,N'-di-(3-phenylpropyl)-2-(t-butoxycarbonylamino)malonamide Prepare by the method of Example 4.1 using 3-phenylpropylamine (0.54 mL, 4.0 mmol). Add Purify by chromatography on silica gel eluting with 2/1 ethyl acetate/hexane to give the title compound (27%).

5.2 Synthesis of N,N'-di-(3-phenylpropyl)-2-aminomalonamide trifluoroacetic acid salt Prepare by the method of Example 4.2 using N,N'-di-(3-phenylpropyl)-2-(t-butoxycarbonylamino)malonamide (0.24 g, 0.53 mmol) to give, after evaporation in vacuo and drying under high vacuum, the title compound.

5.3 Synthesis of N,N'-di-(3-phenylpropyl)-2-((R)-2-bromo-3-phenylpropionylamino)malonamide Prepare by the method of Example 4.3 using N,N'-di-(3-phenylpropyl)-2-aminomalonamide trifluoroacetic acid salt. Purify by chromatography on silica gel eluting with 1/1 ethyl acetate/hexane to give the title compound.

5.4 Synthesis of N,N'-di-(3-phenylpropyl)-2-((S)-2-thioacetyl-3-phenylpropionylamino)malonamide Prepare by the method of Example 4.4 using N,N'-di-(3-phenylpropyl)-2-((R)-2-bromo-3-phenylpropionylamino) malonamide (0.124 g, 0.575 mmol). Purify by chromatography on silica gel eluting with 3/2 ethyl acetate/hexane to give the title compound.

5.5 Synthesis of N,N'-di-(3-phenylpropyl)-2-((S)-2-mercapto-3-phenylpropionylamino)malonamide Prepare by the method of Example 4.5 using N,N'-di-(3-phenylpropyl)-2-((S)-2-thioacetyl-3- phenylpropionylamino)malonamide (0.156 g, 0.289 mmol). After 1 hour, evaporate in vacuo to give a residue. Purify by chromatography on silica gel eluting with 5% acetone/ dichloromethane to give the title compound.

EXAMPLE 6

N,N'-Di-(4-methoxyphenethyl)-2-((S)-2-mercapto-3 -phenylpropionylamino)malonamide

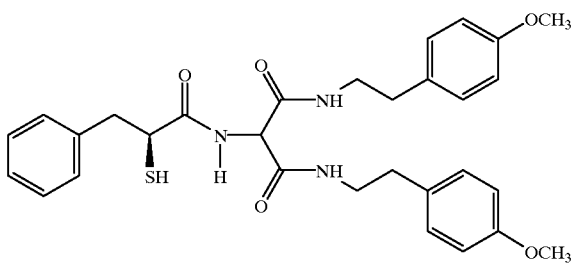

6.1 Synthesis of N,N'-di-(4-methoxyphenethyl)-2-(t-butoxycarbonylamino)malonamide Prepare by the method of Example 4.1 using 4-methoxyphenethylamine (0.585 mL, 3.8 mmol). Add Purify by chromatography on silica gel eluting with 2/1 ethyl acetate/hexane to give the title compound (27%).

6.2 Synthesis of N,N'-di-(4-methoxyphenethyl)-2-aminomalonamide trifluoroacetic acid salt Prepare by the method of Example 4.2 using N,N'-di-(4-methoxyphenethyl)-2-(t-butoxycarbonylamino)malonamide (0.20 g, 0.412 mmol) to give, after evaporation in vacuo and drying under high vacuum, the title compound.

6.3 Synthesis of N,N'-di-(4-methoxyphenethyl)-2-((R)-2-bromo-3-phenylpropionylamino)malonamide Prepare by the method of Example 4.3 using N,N'-di-(4-methoxyphenethyl)-2-aminomalonamide trifluoroacetic acid salt. Purify by chromatography on silica gel eluting with 3/2 ethyl acetate/hexane to give the title compound.

6.4 Synthesis of N,N'-di-(4-methoxyphenethyl)-2-((S)-2-thioacetyl-3-phenylpropionylamino) malonamide Prepare by the method of Example 4.4 using N,N'-di-(4-methoxyphenethyl)-2-((R)-2-bromo-3-phenylpropionylamino)malonamide (0.133 g, 0.223 mmol). Purify by chromatography on silica gel eluting with 3/2 ethyl acetate/hexane to give the title compound (54%).

6.5 Synthesis of N,N'-di-(4-methoxyphenethyl)-2-((S)-2-mercapto-3-phenylpropionylamino) malonamide Prepare by the method of Example 4.5 using N,N'-di-(4-methoxyphenethyl)-2-((S)-2-thioacetyl-3-phenylpropionylamino)malonamide (0.071 g, 0.12 mmol). After 1 hour, evaporate in vacuo to give a residue. Chromatograph the residue on silica gel eluting with 1/1 ethyl acetate/hexane give the title compound.

EXAMPLE 7

N,N'-Dipentyl-2-(2-mercapto-3-phenylpropionylamino)malonamide

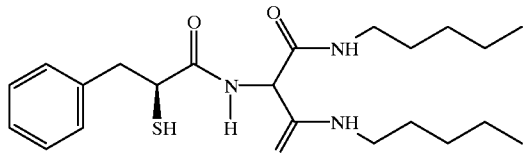

7.1 Synthesis of N,N'-dipentyl-2-(t-butoxycarbonylamino)malonamide

Prepare by the method of Example 4.1 using pentylamine (1.50 mL, 12.8 mmol). Purify by chromatography on silica gel eluting sequentially with 1/1 ethyl acetate/hexane, 3/1 ethyl acetate/hexane, and then 5/1 ethyl acetate/hexane to give the title compound (68%).

7.2 Synthesis of N,N'-dipentyl-2-aminomalonamide trifluoroacetic acid salt

Combine N,N'-dipentyl-2-(t-butoxycarbonylamino) malonamide (1.49 g, 4.17 mmol). After 1.5 hours, evaporate in vacuo and triturate with carbon tetrachloride to give the title compound.

7.3 Synthesis of N,N'-dipentyl-2-((R)-2-bromo-3-phenylpropionylamino)malonamide Prepare by the method of Example 4.3 using N,N'-dipentyl-2-aminomalonamide trifluoroacetic acid salt. Purify by chromatography on silica gel eluting with 3/2 ethyl acetate/hexane to give the title compound.

7.4 Synthesis of N,N'-dipentyl-2-((S)-2-thioacetyl-3-phenylpropionylamino)malonamide Prepare by the method of Example 4.4 using N,N'-dipentyl-2-((R)-2-bromo-3-phenylpropionylamino) malonamide (0.45 g, 0.961 mmol). Purify by chromatography on silica gel eluting with 3/2 ethyl acetate/hexane to give the title compound (62%).

7.5 Synthesis of N,N'-dipentyl-2-((S)-2-mercapto-3-phenylpropionylamino)malonamide Prepare by the method of Example 4.5 using N,N'-dipentyl-2-((S)-2-thioacetyl-3-phenylpropionylamino) malonamide (0.277 g, 0.60 mmol). Purify by chromatograph on silica gel eluting sequentially with 5% acetone/ dichloromethane and then 10% acetone/dichloromethane to give the title compound.

EXAMPLE 8

N,N'-Di-(2-(N-anilino)ethyl)-2-(2-mercapto-3-phenylpropionylamino)malonamide

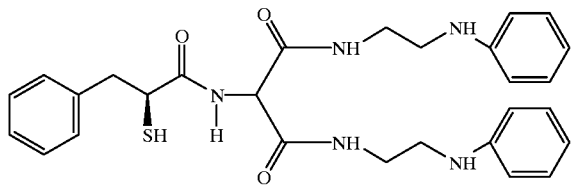

8.1 Synthesis of N,N'-di-(2-(N-anilino)ethyl)-2-(t-butoxycarbonylamino)malonamide Combine t-butoxycarbonylaminomalonic acid (0.730 g, 2.00 mmol), 2-(N-anilino)ethylamine (0.654 mL, 5.00 mmol) N-methylmorpholine (0.55 mL, 5.0 mmol)), 1-ethyl-3-(3-(dimethylamino)propyl)carbodiimide hydrochloric acid salt (0.958 g, 5.0 mmol), and 1-hydroxybenztriazole hydrate (0.67 g, 5.00 mmol) in dichloromethane (10 mL) and tetrahydrofuran (1 mL). After 18 hours, concentrate in vacuo, dilute the concentrated reaction mixture with ethyl acetate and extract with a saturated aqueous sodium bicarbonate solution and then brine. Extract each of the aqueous layers with ethyl acetate. Combine the organic layers, dry over $Na_2SO_4$, filter, and evaporate in vacuo to give a residue. Combine the residue, methanol (10 mL), and celite and apply to a silica gel column. Chromatograph eluting with 3/2 ethyl acetate/hexane to give the title compound (60%).

8.2 Synthesis of N,N'-di-(2-(N-anilino)ethyl)-2-aminomalonamide hydrochloric acid salt Combine N,N'-di-(2-(N-anilino)ethyl)-2-(t-butoxycarbonylamino)malonamide (0.55 g, 1.21 mmol) and tetrahydrofuran (7 mL) and diethyl ether (7 mL). Add a solution of hydrochloric acid in diethyl ether (10 mL, 1 M, 10 mmol) to give a solid. After 45 minutes, collect the solid by filtration to give the title compound.

8.3 Synthesis of N,N'-di-(2-(N-anilino)ethyl)-2-((R)-2-bromo-3-phenylpropionylamino)malonamide Combine N,N'-di-(2-(N-anilino)ethyl)-2-aminomalonamide hydrochloric acid salt (0.474 g, 0.866 mmol) and dichloromethane (10 mL). Add (R)-2-bromo-3-phenylpropionic acid (0.26 g, 1.13 mmol). Add triethylamine (0.426 mL, 3.06 mmol). Add pyridine benzotriazol-1-yloxytris(dimethylamino)phosphonium hexafluorophosphate complex (0.478 g, 1.13 mmol). After 18 hours, evaporate in vacuo and dilute the concentrated reaction mixture with ethyl acetate, extract with an aqueous 5% sulfuric acid solution, a saturated sodium bicarbonate solution, and then brine. Extract each of the aqueous layers with ethyl acetate. Combine the organic layers and dry over $Na_2SO_4$, filter, and evaporate in vacuo to give a residue. Chromatograph the residue on silica gel eluting sequentially with 1/1 ethyl acetate/hexane and then 2/1 ethyl acetate/hexane to give the title compound (62%).

8.4 Synthesis of N,N'-di-(2-(N-anilino)ethyl)-2-((S)-2-thioacetyl-3-phenylpropionylamino)malonamide Prepare by the method of Example 4.4 using N,N'-di-(2-(N-anilino)ethyl)-2-((R)-2-bromo-3-phenylpropionylamino)malonamide (0.311 g, 0.549 mmol) and thioacetic acid (0.08 mL, 0.010 mmol) in dimethylformamide (8 mL), and cesium carbonate (0.18 g, 0.549 mmol). Purify by chromatography on silica gel eluting sequentially with 1/1 ethyl acetate/hexane, 2/1 ethyl acetate/hexane, and then 3/1 ethyl acetate/hexane to give the title compound.

8.5 Synthesis of N,N'-di-(2-(N-anilino)ethyl)-2-((S)-2-mercapto-3-phenylpropionylamino)malonamide Prepare by the method of Example 4.5 using methanol (10 mL) and N,N'-di-(2-(N-anilino)ethyl)-2-((S)-2-thioacetyl-3-phenylpropionylamino)malonamide (0.151 g, 0.269 mmol) in degassed methanol (10 mL) and tetrahydrofuran (7 mL). After 2.5 hour, evaporate in vacuo to give a residue. Chromatograph the residue on silica gel eluting sequentially with 3/2 ethyl acetate/hexane and then 2/1 ethyl acetate/hexane to give the title compound.

Preparation 4

2-(S)-2-Thioacetyl-3-pheynylproionic acid

Combine 2-(R)-2-bromo-3-phenylpropionic acid (2.85 g, 12.4 mmol), thioacetic acid (1.4 mL, 19.5 mmol), and dimethylformamide (30 mL). Degas by repeated cycles of vacuum and filling with nitrogen gas. Add cesium carbonate (4.25 g, 12.4 mmol). After 18 hours, add with an aqueous 5% sulfuric acid solution, dilute with water, and extract four times with ethyl acetate. Extract the combined organic layers with brine, dry over $Na_2SO_4$, filter, and evaporate in vacuo to give a residue. Chromatograph the residue on silica gel eluting sequentially with 1/1/0.02 hexane/ethyl acetate/acetic acid and then 1/1/0.02 hexane/ethyl acetate/acetic acid to give the title compound (43%).

EXAMPLE 9

N,N'-Di-(pydrid-4-ylethyl)-2-(2-mercapto-3-phenylpropionylamino)malonamide

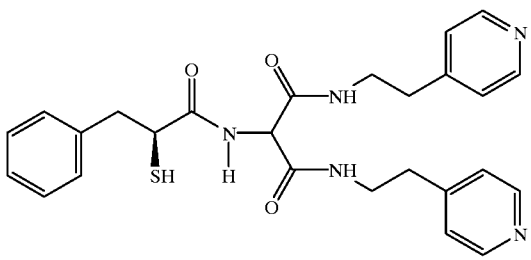

9.1 Synthesis of N,N'-di-(pydrid-4-ylethyl)-2-(t-butoxycarbonylamino)malonamide Combine t-butoxycarbonylaminomalonic acid (0.438 g, 2.0 mmol), 2-(pyrid-4-yl)ethylamine (0.61 g, 5.0 mmol), N-methylmorpholine (0.55 mL, 5.0 mmol)), 1-ethyl-3-(3-(dimethylamino)propyl)carbodiimide hydrochloric acid salt (0.96 g, 5.0 mmol), and 1-hydroxybenztriazole hydrate (0.68 g, 5.0 mmol) in dichloromethane (10 mL) and tetrahydrofuran (1 mL). After 18 hours, concentrate in vacuo, dilute the concentrated reaction mixture with ethyl acetate, and extract with a saturated aqueous sodium bicarbonate solution and then brine. Extract each of the aqueous layers with ethyl acetate. Combine the organic layers, dry over $Na_2SO_4$, filter, and evaporate in vacuo to give a residue. Chromatograph the residue on silica gel eluting with 10% methanol/dichloromethane to give the title compound (80%).

9.2 Synthesis of N,N'-di-(pydrid-4-ylethyl)-2-aminomalonamide hydrochloric acid salt Combine N,N'-di-(pydrid-4-ylethyl)-2-(t-butoxycarbonylamino)malonamide (0.686 g, 1.61 mmol) and diethyl ether (20 mL). Add a solution of hydrochloric acid in diethyl ether (10 mL, 1 M, 10 mmol). After 1 hour, evaporate in vacuo to give the title compound.

9.3 Synthesis of N,N'-di-(pydrid-4-ylethyl)-2-((R)-2-thioacetyl-3-phenylpropionylamino)malonamide Combine N,N'-di-(pydrid-4-ylethyl)-2-aminomalonamide hydrochloric acid salt (0.669 g, 1.63 mmol) and dichloromethane (10 mL), tetrahydrofuran (5 mL), and dimethylformamide (3 mL). Add a solution of (S)-2-thioacetyl-3-phenylpropionic acid (0.43 g, 1.9 mmol) in dichloromethane (1.9 mL). Add N-methylmorpholine (0.357 mL, 4.90 mmol), 1-ethyl-3-(3-(dimethylamino)propyl)carbodiimide hydrochloric acid salt (0.343 g, 1.8 mmol), and 1-hydroxybenztriazole hydrate (0.242 g, 0.18 mmol). After 18 hours, dilute the reaction mixture with ethyl acetate, extract with a saturated aqueous sodium bicarbonate solution, and then brine to give a residue. Chromatograph the residue on silica gel eluting sequentially with 10% methanol/dichloromethane and then 15% methanol/dichloromethane to give the title compound (63%).

9.4 Synthesis of N,N'-di-(pydrid-4-ylethyl)-2-((S)-2-mercapto-3-phenylpropionylamino)malonamide Prepare by the method of Example 4.5 using methanol (15 mL) and N,N'-di-(pydrid-4-ylethyl)-2-((S)-2-thioacetyl-3-phenylpropionylamino)malonamide (0.543 g, 1.02 mmol) in degassed methanol (15 mL). After 1.5 hours, evaporate in vacuo to give a residue. Chromatograph the residue on silica gel eluting with 1/10 methanol/dichloromethane to give the title compound.

EXAMPLE 10

N,N'-Diphenethyl-2-((S)-2-mercaptopropionylamino)malonamide

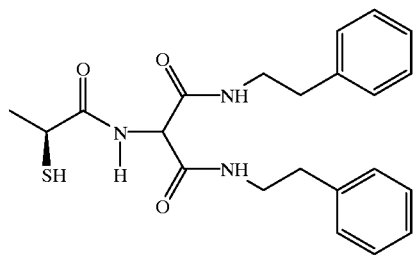

10.1 Synthesis of N,N'-diphenethyl-2-((R)-2-bromopropionylamino)malonamide

Prepare by the method of Example 4.3 using (R)-2-bromopropionic acid (0.109 mL, 1.2 mmol). Purify by chromatography on silica gel eluting with 3/2 ethyl acetate/hexane to give the title compound.

10.2 Synthesis of N,N'-diphenethyl-2-((S)-2-thioacetylpropionylamino)malonamide Prepare by the method of Example 4.4 using N,N'-diphenethyl-2-((R)-2-bromopropionylamino)malonamide (0.175 g, 0.38 mmol). Purify by chromatography on silica gel eluting with 3/2 ethyl acetate/hexane to give the title compound (76%).

10.3 Synthesis of N,N'-diphenethyl-2-((S)-2-mercaptopropionylamino)malonamide Prepare by the method of Example 1.5 using N,N'-diphenethyl-2-((R)-2-thioacetylpropionylamino)malonamide (0.131 g, 0.29 mmol). Purify by chromatography on silica gel eluting with 3/2 ethyl acetate/hexane to give the title compound (98%).

EXAMPLE 11

N,N'-Diphenethyl-2-(2-mercaptopropionylamino)malonamide

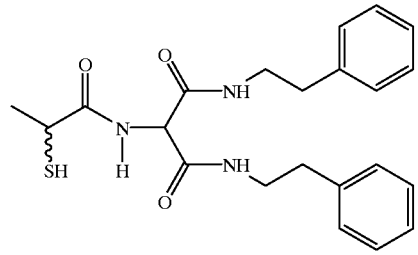

11.1 Synthesis of N,N'-diphenethyl-2-(2-bromopropionylamino)malonamide

Prepare by the method of Example 4.3 using 2-bromopropionic acid (0.108 mL, 1.2 mmol). Purify by chromatography on silica gel eluting with 3/2 ethyl acetate/hexane to give the title compound.

11.2 Synthesis of N,N'-diphenethyl-2-(2-thioacetylpropionylamino)malonamide Prepare by the method of Example 4.4 using N,N'-diphenethyl-2-(2-bromopropionylamino)malonamide (0.152 g, 0.33 mmol). Purify by chromatography on silica gel eluting with 3/2 ethyl acetate/hexane to give the title compound (96%).

11.3 Synthesis of N,N'-diphenethyl-2-(2-mercaptopropionylamino)malonamide

Prepare by the method of Example 1.5 using N,N'-diphenethyl-2-(2-thioacetylpropionylamino)malonamide (0.131 g, 0.29 mmol). Purify by chromatography on silica gel eluting with 3/2 ethyl acetate/hexane to give the title compound (100%).

EXAMPLE 12

N,N'-Diphenethyl-2-(2-mercaptopentanoylamino)malonamide

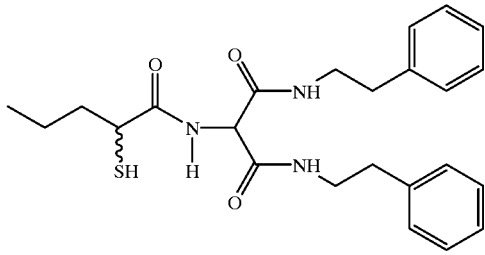

12.1 Synthesis of N,N'-diphenethyl-2-(2-bromopentanoylamino)malonamide

Prepare by the method of Example 4.3 using 2-bromopentanoic acid (0.16 mL, 1.2 mmol). Purify by chromatography on silica gel eluting with 1/1 ethyl acetate/hexane to give the title compound.

12.2 Synthesis of N,N'-diphenethyl-2-(2-thioacetylpentanoylamino)malonamide

Prepare by the method of Example 4.4 using N,N'-diphenethyl-2-(2-bromopentanoylamino)malonamide (0.162 g, 0.33 mmol). Purify by chromatography on silica gel eluting with 3/2 ethyl acetate/hexane to give the title compound (96%).

12.3 Synthesis of N,N'-diphenethyl-2-(2-mercaptopentanoylamino)malonamide

Prepare by the method of Example 1.5 using N,N'-diphenethyl-2-(2-thioacetylpentanoylamino)malonamide (0.131 g, 0.29 mmol). Purify by chromatography on silica gel eluting with sequentially with 2/3 ethyl acetate/hexane and then 1/1 ethyl acetate/hexane to give the title compound.

Preparation 5

2-((S)-2-(p-methoxybenzylmercapto)-3-phenylpropionylamino)malonic acid

Combine (R)-2-bromo-3-phenylpropionic acid (3.44 g, 15 mmol), diethyl aminomalonate hydrochloride (4.23 g, 20 mmol), and N-methylmorpholine (5.5 mL, 50 mmol) in dichloromethane (50 mL). Add 1-ethyl-3-(3-(dimethylamino)propyl)carbodiimide hydrochloric acid salt (3.83 g, 20 mmol) and 1-hydroxybenztriazole hydrate (2.70 g, 20 mmol). Add tetrahydrofuran (10 mL). After 20 hours, concentrate in vacuo and partition the concentrated reaction mixture between an aqueous 5% sulfuric acid solution and methyl t-butyl ether. Separate the layers and extract the organic layer with a saturated aqueous sodium bicarbonate solution and then brine. Dry the organic layer over $Na_2SO_4$, filter, and evaporate in vacuo to give a residue. Chromatograph the residue on silica gel eluting sequentially with 1/4 ethyl acetate/hexane, 1/3 ethyl acetate/hexane, and then 2.5/1 ethyl acetate/hexane to give diethyl 2-((R)-2-bromo-3-phenylpropionylamino)malonate.

Combine diethyl 2-((R)-2-bromo-3-phenylpropionylamino)malonate (3.15 g, 8.16 mmol) and 4-methyoxybenzylmercaptan (2.6 mL, 19 mmol), and dimethylformamide (25 mL). Degas by repeatedly applying vacuum and filling the vessel with nitrogen. Add cesium carbonate (2.94 g, 9.9 mmol). After 16 hours, partition the reaction mixture between water and diethyl ether. Extract the organic layer with brine, dry over $Na_2SO_4$, filter, and evaporate in vacuo to give a residue. Chromatograph the residue on silica gel eluting sequentially with 3/1 hexane/ethyl acetate and then 2/1 hexane/ethyl acetate to give diethyl 2-((S)-2-(p-methoxybenzymercapto)-3-phenylpropionylamino)malonate.

Combine diethyl 2-((S)-2-(p-methoxybenzymercapto)-3-phenylpropionylamino) malonate (3.15 g, 6.85 mmol) and an aqueous 6 M sodium hydroxide solution (4.6 mL, 28 mmol) in ethanol (15 mL). After 24 hours, concentrate in vacuo, dilute the concentrated reaction mixture with water, adjust the pH to about 2.5 using an aqueous 6 M hydrochloric acid solution, and lyophilize to give the title compound and sodium chloride.

EXAMPLE 13

N,N'-Di-(4-chlorophenethyl)-2-(2-mercapto-3-phenylpropionylamino)malonamide

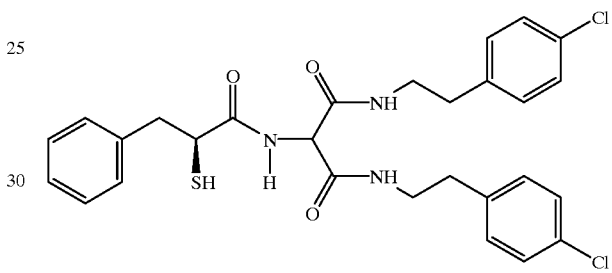

13.1 Synthesis of N,N'-di-(4-chlorophenethyl)-2-((S)-2-(p-methoxybenzylmercapto)-3-phenylpropionylamino)malonamide Combine 2-((S)-2-(p-methoxybenzylmercapto)-3-phenylpropionylamino)malonic acid (prepared by the method of Preparation 5, 0.476 g, 63% acid/37% sodium chloride, 0.74 mmol), dichloromethane (9 mL), and tetrahydrofuran (1.5 mL). Add 4-chlorophenylethylamine (0.31 mL, 2.23 mmol), N-methylmorpholine (0.25 mL, 2.3 mmol), 1-ethyl-3-(3-(dimethylamino)propyl)carbodiimide hydrochloric acid salt (0.427 g, 2.23 mmol) and 1-hydroxybenztriazole hydrate (0.301 g, 2.23 mmol). After 3 days, concentrate in vacuo and partition the concentrated reaction mixture between an aqueous 5% sulfuric acid solution and ethyl acetate. Separate the layers and extract the organic layer with a saturated aqueous sodium bicarbonate solution and then brine. Dry the organic layer over $Na_2SO_4$, filter, and evaporate in vacuo to give a residue. Chromatograph the residue on silica gel eluting sequentially with 2/3 ethyl acetate/hexane, 1/1 ethyl acetate/hexane, and then 1/2 ethyl acetate/hexane to give the title compound.

13.2 Synthesis of N,N'-di-(4-chlorophenethyl)-2-(2-mercapto-3-phenylpropionylamino)malonamide Combine of N,N'-di-(4-chlorophenethyl)-2-((S)-2-(p-methoxybenzylmercapto)-3-phenylpropionylamino)malonamide (0.29 g, 0.43 mmol), mercury (II) acetate (0.171 g, 0.54 mmol), and anisole (0.47 mL) in dichloromethane (10 mL). Cool in an ice bath and degas by repeatedly applying vacuum and filling the vessel with nitrogen. Add trifluoroacetic acid (4 mL). After 3 hours, purge with hydrogen sulfide (gas) for about 10 minutes. Filter and evaporate in vacuo to give a residue. Triturate the residue with diethyl ether to give the title compound as a solid (80%).

EXAMPLE 14

N,N'-Di-(2-methoxyphenethyl)-2-((S)-2-mercapto-3-phenylpropionylamino)malonamide

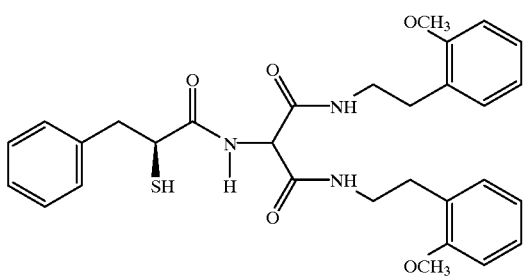

14.1 Synthesis of N,N'-di-(2-methoxyphenethyl)-2-((S)-2-(p-methoxybenzylmercapto)-3-phenylpropionylamino)malonamide Prepare by the method of Example 13.1 using 2-methoxyphenylethylamine (0.31 mL, 2.23 mmol). Purify by chromatography on silica gel eluting sequentially with 2/3 ethyl acetate/hexane and then 1/2 ethyl acetate/hexane to give the title compound (50%).

14.2 Synthesis of N,N'-di-(2-methoxyphenethyl)-2-((S)-2-mercapto-3-phenylpropionylamino)malonamide Prepare by the method of Example 13.2 using N,N'-di-(2-methoxyphenethyl)-2-((S)-2-(p-methoxybenzylmercapto)-3-phenylpropionylamino)malonamide (0.24 g, 0.37 mmol). Purify by chromatography on silica gel eluting with 2/3 ethyl acetate/hexane to give the title compound (91%).

EXAMPLE 15

N,N'-Di-(4-methylphenethyl)-2-((S)-2-mercapto-3-phenylpropionylamino)malonamide

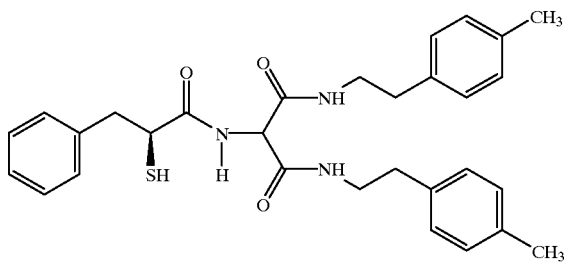

15.1 Synthesis of N,N'-di-(2-methylphenethyl)-2-((S)-2-(p-methoxybenzylmercapto)-3-phenylpropionylamino)malonamide Combine 2-((S)-2-(p-methoxybenzylmercapto)-3-phenylpropionylamino)malonic acid (prepared by the method of Preparation 5, 0.476 g, 63% acid/37% sodium chloride, 0.74 mmol), and N-methylmorpholine (0.27 mL, 2.4 mmol), 2-methylphenylethylamine (0.25 mL, 1.7 mmol), dichloromethane (9 mL), and tetrahydrofuran (1mL). Add, 1-ethyl-3-(3-(dimethylamino)propyl) carbodiimide hydrochloric acid salt (0.314 g, 1.64 mmol) and 1-hydroxybenztriazole hydrate (0.22 g, 1.64 mmol). After 1 day, concentrate in vacuo and partition the concentrated reaction mixture between an aqueous 5% sulfuric acid solution and ethyl acetate. Separate the layers and extract the organic layer with a saturated aqueous sodium bicarbonate solution and then brine. Dry the organic layer over $Na_2SO_4$, filter, and evaporate in vacuo to give a residue. Chromatograph the residue on silica gel eluting sequentially with 2/3 ethyl acetate/hexane and then 2/1 ethyl acetate/hexane to give the title compound.

15.2 Synthesis of N,N'-di-(2-methylphenethyl)-2-((S)-2-mercapto-3-phenylpropionylamino)malonamide Combine of N,N'-di-(2-methylphenethyl)-2-((S)-2-(p-methoxybenzylmercapto)-3-phenylpropionylamino)malonamide (0.175 g, 0.274 mmol), mercury (II) acetate (0.108 g, 0.34 mmol), and anisole (0.3 mL) in dichloromethane (10 mL). Cool in an ice bath and degas by repeatedly applying vacuum and filling the vessel with nitrogen. Add trifluoroacetic acid (4 mL). After 3 hours, purge with hydrogen sulfide (gas) for about 10 minutes. Filter and evaporate in vacuo to give a residue. Combine the residue with carbon tetrachloride and evaporate in vacuo to remove most of the trifluoroacetic acid. Chromatograph the residue on silica gel eluting with 1/2 ethyl acetate/hexane and then 1/1 ethyl acetate/hexane to give the title compound.

EXAMPLE 16

N,N'-Di-(3-methoxyphenethyl)-2-(2-mercapto-3-phenylpropionylamino)malonamide

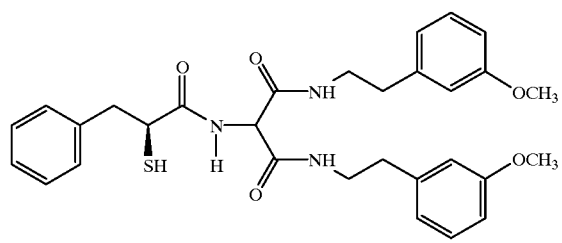

16.1 Synthesis of N,N'-di-(3-methoxyphenethyl)-2-((S)-2-(p-methoxybenzylmercapto)-3-phenylpropionylamino)malonamide Prepare by the method of Example 15.1 using 3-methoxyphenylethylamine (0.24 mL, 1.7 mmol). Purify by chromatography on silica gel eluting sequentially with 2/3 ethyl acetate/hexane and then 2/1 ethyl acetate/hexane to give the title compound.

16.2 Synthesis of N,N'-di-(3-methoxyphenethyl)-2-((S)-2-mercapto-3-phenylpropionylamino)malonamide Prepare by the method of Example 15.2 using N,N'-di-(3-methoxyphenethyl)-2-((S)-2-(p-methoxybenzylmercapto)-3-phenylpropionylamino)malonamide (0.181 g, 0.27 mmol). Purify by chromatography on silica gel eluting with 1/2 ethyl acetate/hexane and then 1/1 ethyl acetate/hexane to give the title compound.

EXAMPLE 17

N,N'-Di-(3,4-dimethoxyphenethyl)-2-((S)-2-mercapto-3-phenylpropionylamino)malonamide

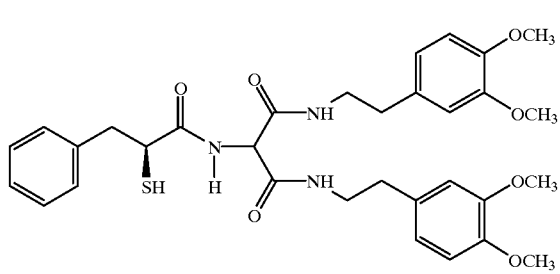

17.1 Synthesis of N,N'-di-(3,4-dimethoxyphenethyl)-2-((S)-2-(p-methoxybenzylmercapto)-3-phenylpropionylamino) malonamide Combine 2-((S)-2-(p-methoxybenzylmercapto)-3-phenylpropionylamino)malonic acid (prepared by the method of Preparation 5, 0.476 g, 63% acid/37% sodium chloride, 0.74 mmol), and N-methylmorpholine (0.27 mL, 2.4 mmol), 3,4-dimethoxyphenylethylamine hydrochloride (0.50 g, 2.3 mmol), dichloromethane (9 mL), and tetrahydrofuran (1 mL). Cool in an ice bath. Add, 1-ethyl-3-(3-(dimethylamino)propyl)carbodiimide hydrochloric acid salt (0.314 g, 1.64 mmol) and 1-hydroxybenztriazole hydrate (0.22 g, 1.64 mmol). After 1 day, concentrate in vacuo and partition the concentrated reaction mixture between an aqueous 5% sulfuric acid solution and ethyl acetate. Separate the layers and extract the organic layer with a saturated aqueous sodium bicarbonate solution and then brine. Dry the organic layer over Na$_2$SO$_4$, filter, and evaporate in vacuo to give a residue. Chromatograph the residue on silica gel eluting sequentially with 2/1 dichloromethane/ethyl acetate and then 1/1 dichloromethane/ethyl acetate to give the title compound.

17.2 Synthesis of N,N'-di-(3,4-dimethoxyphenethyl)-2-((S)-2-mercapto-3-phenylpropionylamino)malonamide Combine of N,N'-di-(3,4-dimethoxyphenethyl)-2-((S)-2-(p-methoxybenzylmercapto)-3-phenylpropionylamino) malonamide (0.139 g, 0.19 mmol), mercury (II) acetate (0.076 g), and anisole (0.3 mL), and veratrole (0.24 mL) in dichloromethane (10 mL). Cool in an ice bath and degas by repeatedly applying vacuum and filling the vessel with nitrogen. Add trifluoroacetic acid (4 mL). After 3 hours, purge with hydrogen sulfide (gas) for about 10 minutes. Filter and evaporate in vacuo to give a residue. Chromatograph the residue on silica gel eluting with 3/1 dichloromethane/ethyl acetate/hexane and then 3/2 dichloromethane/ethyl acetate to give the title compound.

EXAMPLE 18

N,N'-Di-(3-chlorophenethyl)-2-(2-mercapto-3-phenylpropionylamino)malonamide

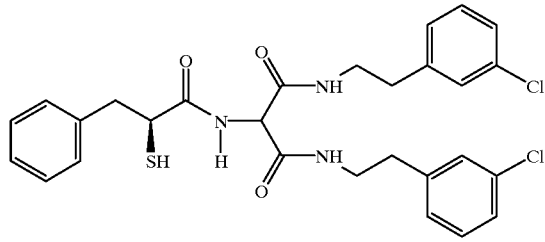

18.1 Synthesis of N,N'-di-(3-chlorophenethyl)-2-((S)-2-(p-methoxybenzylmercapto)-3-phenylpropionylamino)malonamide Prepare by the method of Example 17.1 using 3-chlorophenylethylamine hydrochloride (0.50 g, 2.6 mmol). Purify by chromatography on silica gel eluting sequentially with 3/2 hexane/ethyl acetate and then 1/2 hexane/ethyl acetate to give the title compound.

18.2 Synthesis of N,N'-di-(3-chlorophenethyl)-2-(2-mercapto-3-phenylpropionylamino)malonamide Prepare by the method of Example 15.2 using N,N'-di-(3-chlorophenethyl)-2-((S)-2-(p-methoxybenzylmercapto)-3-phenylpropionylamino)malonamide (0.126 g, 0.186 mmol). Purify by chromatography on silica gel eluting sequentially with 2/1 hexane/ethyl acetate and then 1/1 hexane/ethyl acetate to give the title compound.

EXAMPLE 19

N,N'-Di-(3,4-dichlorophenethyl)-2-(2-mercapto-3-phenylpropionylamino)malonamide

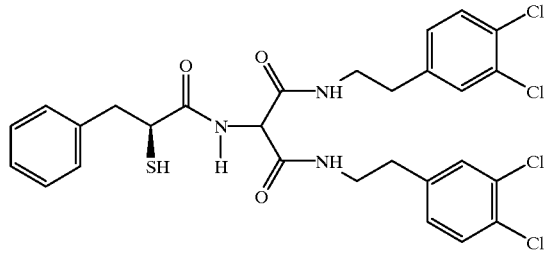

19.1 Synthesis of N,N'-di-(3,4-dichlorophenethyl)-2-((S)-2-(p-methoxybenzylmercapto)-3-phenylpropionylamino)malonamide Prepare by the method of Example 17.1 using 3.4-dichlorophenylethylamine hydrochloride (0.50 g, 2.2 mmol). Purify by chromatography on silica gel eluting sequentially with 3/2 hexane/ethyl acetate and then 1/2 hexane/ethyl acetate to give the title compound.

19.2 Synthesis of N,N'-di-(3,4-dichlorophenethyl)-2-(2-mercapto-3-phenylpropionylamino)malonamide Prepare by the method of Example 15.2 using N,N'-di-(3,4-dichlorophenethyl)-2-((S)-2-(p-methoxybenzylmercapto)-3-phenylpropionylamino)

malonamide (0.166 g, 0.222 mmol). Coevaporation with carbon tetrachloride gives the title compound.

Preparation 6

Synthesis of (R)-2-bromo-6-phthalimidohexanoic acid

Combine (R)-2-N-carbobenzyloxy-6-aminohexanoic acid ((R)-Na-Cbz-lysine) (14.0 g, 50 mmol) and water (500 mL). Add sodium carbonate (5.65 g, 53 mmol) and N-carbethoxyphthalimide (13.15 g, 60 mmol). After 1.5 hours, acidify using aqueous 12M hydrochloric acid to give a solid. Collect the solid by filtration, rinse with water, and dry to give (R)-2-N-carbobenzyloxy-6-phthalamidohexanoic acid.

Combine (R)-2-N-carbobenzyloxy-6-phthalamidohexanoic acid obtained above, methanol (200 mL), 10% palladium-on-carbon (1 g) and treat with hydrogen at atmospheric pressure. After 18 hours, filter, add to the filtrate a solution of hydrochloric acid in methanol (50 mL, 1 M, 50 mmol), and evaporate in vacuo to give (R)-2-amino-6-phthalamidohexanoic acid hydrochloric acid salt.

EXAMPLE 20

N,N'-Diphenethyl-2-((S)-2-mercapto-6-phthalimidohexanoylamino)malonamide

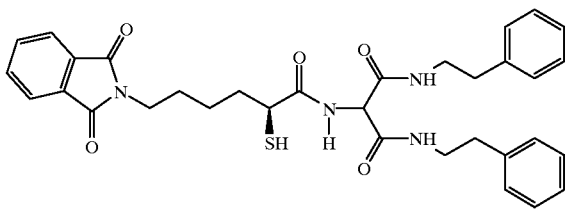

20.1 Synthesis of N,N'-diphenethyl-2-((S)-2-bromo-6-phthalimidohexanoylamino)malonamide Prepare by the method of Example 3.3 using N,N'-diphenethyl-2-aminomalonamide trifluoroacetic acid salt (20 mmol) and (R)-2-bromo-6-phthalimidohexanoic acid (25 mmol) to give the title compound.

20.2 Synthesis of N,N'-diphenethyl-2-((S)-2-(p-methoxybenzylmercapto)-6-phthalimidohexanoylamino)malonamide Combine N,N'-diphenethyl-2-((S)-2-bromo-6-phthalimidohexanoylamino)malonamide (10 mmol), 4-methyoxybenzylmercaptan (3.48 mL, 25 mmol), and tetrabutylammonium iodide (about 50 mg) in dimethylformamide (10 mL). Degas by repeatedly applying vacuum and filling the vessel with nitrogen. Add cesium carbonate (4.10 g, 12.5 mmol). After 15 hours, partition the reaction mixture between water and methyl t-butyl ether, saturate the aqueous layer with sodium chloride. Extract the aqueous layer with brine, dry over $Na_2SO_4$, filter, and evaporate in vacuo to give the title compound.

20.3 Synthesis of N,N'-diphenethyl-2-((S)-2-mercapto-6-phthalimidohexanoylamino)malonamide Prepare by the method of Example 15.2 using N,N'-diphenethyl-2-((S)-2-(p-methoxybenzylmercapto)-6-phthalimidohexanoylamino)malonamide (5 mmol) to give the title compound.

The present invention provides a method of inhibiting matrix metalloproteinase (MMP) to a patient in need thereof comprising administering to the patient an effective matrix metalloproteinase inhibiting amount of a compound of formula (1).

As used herein, the term "patient" refers to warm-blooded animals or mammals, including guinea pigs, dogs, cats, rats, mice, hamsters, rabbits and primates, including humans. A patient is in need of treatment to inhibit MMP when it would be beneficial to the patient to reduce the physiological effect of active MMP. For example, a patient is in need of treatment to inhibit MMP when a patient is suffering from a disease state characterized by excessive tissue disruption or tissue degradation, such as, but not limited to, a neoplastic disease state or cancer; rheumatoid arthritis; osteoarthritis; osteoporosis; cardiovascular disorders, such as atherosclerosis; corneal ulceration; dental diseases, such as gingivitis or periodontal disease; and neurological disorders, such as multiple sclerosis; chronic inflammatory disorders, such as emphysema and especially smoking-induced emphysema.

The identification of those patients who are in need of treatment to inhibit MMP is well within the ability and knowledge of one skilled in the art. A clinician skilled in the art can readily identify, by the use of clinical tests, physical examination and medical/family history, those patients who are suffering from disease states characterized by excessive tissue disruption or tissue degradation.

An "effective matrix metalloproteinase inhibiting amount" of a compound of formula (1) is an amount which is effective, upon single or multiple dose administration to the patient, in providing relief of symptoms associated with MMP and is thus effective in inhibiting MMP-induced tissue disruption and/or MMP-induced tissue degradation. As used herein, "relief of symptoms" of MMP-mediated conditions refers to decrease in severity over that expected in the absence of treatment and does not necessarily indicate a total elimination or cure of the disease. Relief of symptoms is also intended to include prophylaxis.

An effective matrix metalloproteinase inhibiting dose can be readily determined by the use of conventional techniques and by observing results obtained under analogous circumstances. In determining the effective dose, a number of factors are considered including, but not limited to: the species of the patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

An effective matrix metalloproteinase inhibiting amount of a compound of formula (1) will generally vary from about 0.1 milligram per kilogram of body weight per day (mg/kg/day) to about 300 milligrams per kilogram of body weight per day (mg/kg/day). A daily dose of from about 1 mg/kg to about 100 mg/kg is preferred.

A neoplastic disease state refers to an abnormal state or condition characterized by rapidly proliferating cell growth or neoplasm. Neoplastic disease states for which treatment with a compound of formula (1) will be particularly useful include: Leukemias, such as, but not limited to, acute lymphoblastic, chronic lymphocytic, acute myeloblastic and chronic myelocytic; Carcinomas and adenocarcinomas, such as, but not limited to, those of the cervix, oesophagus, stomach, small intestines, colon, lungs (both small and large cell), breast and prostate; Sarcomas, such as, but not limited to, oesteroma, osteosarcoma, lipoma, liposarcoma, hemangioma and hemangiosarcoma; Melanomas, including amelanotic and melanotic; and mixed types of neoplasias such as, but not limited to carcinosarcoma, lymphoid tissue type, follicullar reticulum, cell sarcoma and Hodgkin's Disease. Neoplastic disease states for which treatment with a compound of formula (1) will be particularly preferred include carcinomas and adenocarcinomas, particularly of the breast, prostate and lung.

Atherosclerosis is a disease state characterized by the development and growth of atherosclerotic lesions or plaque. The identification of those patients who are in need of treatment for atherosclerosis is well within the ability and knowledge of one of ordinary skill in the art. For example, individuals who are either suffering from clinically significant atherosclerosis or who are at risk of developing clinically significant atherosclerosis are patients in need of treatment for atherosclerosis. A clinician of ordinary skill in the art can readily determine, by the use of clinical tests, physical examination and medical/family history, if an individual is a patient in need of treatment for atherosclerosis.

The term "chronic inflammatory disease" refers to diseases or conditions characterized by persistent inflammation in the absence of an identifiable irritant or microbial pathogen. Inflammatory diseases for which treatment with a compound of formula (1) will be particularly useful include: emphysema, chronic bronchitis, asthma, and chronic inflammation, and especially smoking-induced emphysema.

In effecting treatment of a patient, a compound of formula (1) can be administered in any form or mode which makes the compound bioavailable in effective amounts, including oral and parenteral routes. For example, the compound can be administered orally, subcutaneously, intramuscularly, intravenously, transdermally, topically, intranasally, rectally, inhalation, and the like. Oral and inhalation administration is generally preferred. One skilled in the art of preparing formulations can readily select the proper form and mode of administration depending upon the disease state to be treated, the stage of the disease, and other relevant circumstances. *Remington's Pharmaceutical Sciences,* 18th Edition, Mack Publishing Co. (1990).

A compound of formula (1) can be administered in the form of pharmaceutical compositions or medicaments which are made by combining a compound of formula (1) with pharmaceutically acceptable carriers or excipients, the proportion and nature of which are determined by the chosen route of administration, and standard pharmaceutical practice.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, gels, ointments, aerosol or the like.

The pharmaceutical compositions may be administered orally, for example, with an inert diluent or with an edible carrier. They may be enclosed in gelatin capsules or compressed into tablets. For the purpose of oral therapeutic administration, a compound of formula (1) may be incorporated with excipients and used in the form of tablets, troches, capsules, elixirs, suspensions, syrups, wafers, chewing gums and the like. These preparations should contain at least 4% of a compound of formula (1), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound of the invention, but may be varied to be between 0.1% and about 50% of the weight thereof. The amount of the active ingredient present in such compositions is such that a suitable dosage will be obtained. Preferred compositions and preparations are able to be determined by one skilled in the art.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

The compounds of the present invention may also be administered by inhalation, such as by aerosol or dry powder. Delivery may be by a liquefied or compressed gas or a suitable pump system which dispenses the compounds of the present invention or a formulation thereof. Formulations for administration by inhalation of compounds of formula (1) may be delivered in single phase, bi-phasic, or tri-phasic systems. A variety of systems are available for the administration by aerosol of the compounds of formula (1). Dry powder formulations are prepared by either pelletizing or milling the compound of formula (1) to a suitable particle size or by admixing the pelletized or milled compound of formula (1) with a suitable carrier material, such as lactose and the like. Delivery by inhalation includes the necessary container, activators, valves, subcontainers, and the like. Preferred aerosol and dry powder formulations for administration by inhalation can be determined by one skilled in the art.

The MMP inhibitors of the present invention can be evaluated by the procedures that follow.

EXAMPLE A

Source and Activation of proMMP-1

ProMMP-1 (EC 3.4.24.7; interstitial collagenase) was purified from culture medium of human rheumatoid synovial fibroblasts stimulated with macrophage-conditioned medium according to Okada, Y. et al., *J. Biol. Chem.* 261, 14245–14255 (1986). The active MMP-1 was obtained by treatment of proMMP-1 with trypsin (5 µg/mL) at 37° C. for 30 minutes, followed by addition of soybean trypsin inhibitor (50 µg/mL).

Determination of Inhibition Constant ($K_i$) for MMP-1

The activated MMP-1 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in 2.0 mL of assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$328 nm, $\lambda_{em}$393 nm, excitation slit 2.5, emission slit 10). Substrate and inhibitor stock solutions were made in DMF. For determination of $K_i$ values for MMP-1 inhibitors, a series of intermediate inhibitor solutions were prepared in DMF and 1 or 2 µL of the diluted inhibitor solution was mixed with 1 µL of 2 mM substrate solution in DMF in a quartz cuvette containing 2 mL of assay buffer. The enzyme (10 µL of 0.2 µM MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 µM (<<Km) and [MMP-1]=0.8 nM. Under these conditions, the measured $K_{i, app}$ is close to true $K_i$.

Calculation of $K_i$ Values

The $K_i$ for a competitive inhibitor is calculated using: $v_0/v_i=(1+[I]/K_{i, app})$ and $K_i=K_{i, app}/(1+[S]/K_m)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

EXAMPLE B

Source and Activation of proMMP-2

Recombinant MMP-2 was purified from the fermentation broth of yeast *Pichia pastoris* that carries the integrated MMP-2 gene into its chromosome. In brief, the full-length cDNA for MMP-2 was obtained by reverse transcription of RNA from human melanoma A375M cell line by the reverse transcriptase polymerase chain reaction (RT-PCR) using sequence specific oligonucleotides. The nucleotide sequence was confirmed by Taq cycle sequencing. The cDNA was ligated into the *Pichia pastoris* expression vector pHIL-D2 in such a way that the expression of pro-MMP-2 is under the control of the methanol inducible alcohol oxidase promoter. The expression construct was digested with either SalI or NsiI and used to transform the *Pichia pastoris* strains KM71 and SMD1168. A large-scale culture of a selected clone designated 24S was performed in a high cell density fermentor and the recombinant MMP-2 was purified from the culture supernatant by gelatin-sepharose 4B (Pharmacia). The enzyme is sufficiently pure at this stage for routine measurement of inhibition. If desired, however, the enzyme may be further purified by AcA 44 gel filtration (Spectra).

Determination of Inhibition Constant ($K_i$) for MMP-2

The active MMP-2 was obtained by activation of proMMP-2 at 37° C. for 1 h with 4-aminophenylmercuric acetate which was then removed by a Sephadex G-50 spin column. The enzyme is assayed using a fluorogenic substrate, Mca-Pro-Leu-Gly-Leu-Dpa-Ala-Arg-NH$_2$, at 37° C. in 2.0 mL of assay buffer containing 50 mM Tris, pH 7.6, 0.2 M sodium chloride, 50 mM calcium chloride, 0.02% Brij-35, and 50 µM β-mercaptoethanol. The increase in fluorescence is monitored ($\lambda_{ex}$328 nm, $\lambda_{em}$393 nm). Substrate and inhibitor stock solutions are made in DMF. The enzyme is added at the last to start the reaction. For routine measurement of a $K_i$ value for a reversible, competitive inhibitor, the initial rates in the presence of at least four inhibitor concentrations (two inhibitor concentrations above $K_i$ and two below $K_i$) are measured using [S]=1 µM (<<Km) and [MMP-2]=0.4 nM. Under these conditions, the measured $K_i$, app is close to true $K_i$.

EXAMPLE C

Source and Activation of proMMP-3

ProMMP-3 (EC 3.4.24.17; Stromelysin-1) was purified from culture medium of human rheumatoid synovial fibroblasts stimulated with macrophage-conditioned medium according to Okada, Y. et al., *J. Biol. Chem.* 261, 14245-14255 (1986). The active MMP-3 was obtained by treatment of proMMP-3 with trypsin (5 µg/mL) at 37° C. for 30 minutes, followed by addition of soybean trypsin inhibitor (50 µg/mL). Aliquots of the activated MMP-3 were stored at −20° C.

Determination of Inhibition Constant ($K_i$) for MMP-3

The activated MMP-3 is assayed using a fluorogenic substrate, Mca-Pro-Leu-Gly-Leu-Dpa-Ala-Arg-NH$_2$, Knight, C. G. et al., *FEBS Lett.* 296, 263–266 (1992), at 37° C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-3 was monitored with Perkin-Elmer LS50B Fluorimeter ($\lambda_{ex}$ 328 nm, $\lambda_{em}$ 393 nm, excitation slit 2.5, emission slit 10). Substrate and inhibitor stock solutions were made in DMF and 0.1% HCl-DMF, respectively. For determination of $K_i$ values for MMP-3 inhibitors, a series of intermediate inhibitor solutions were prepared in 0.1% HCl-DMF and 1 or 2 µL of the diluted inhibitor solution was mixed with 1 µL of 2 mM substrate solution in DMF in a quartz cuvette containing 2 mL of assay buffer. The enzyme (10 µL of 0.2 µM MMP-3 dilution in assay buffer) was added at the last to start the reaction. For routine measurement of a $K_i$ value for a reversible, competitive inhibitor, the initial rates in the presence of at least four inhibitor concentrations (two concentrations above $K_i$ and two concentrations below $K_i$) were measured using [S]=1 µM (<<$K_m$) and [MMP-3]=1 nM. Under these conditions, the measured $K_{i, app}$ is close to true $K_i$.

Calculation of $K_i$ Values

The $K_i$ for a competitive inhibitor is calculated using: $v_0/v_i=(1+[I]/K_{i, app})$ and $K_i=K_{i, app}/(1+[S]/K_m)$, where $v_0$ is the initial rate in the absence of inhibitor, $v_i$ is the initial rate in the presence of inhibitor at the concentration of [I], [S] is the substrate concentration, and $K_m$ is the Michaelis constant. If slow binding is observed (i.e. if the approach to the binding equilibrium is slow), the final steady-state rate rather than the initial rate is taken as $v_i$.

EXAMPLE D

Source of MMP-12 (macrophage metalloelastase)

MMP-12 (EC 3.4.24.65) was cloned, expressed and purified according to Shapiro, S. D. et al., *J Biol. Chem.* 268, 23824–23829 (1993). Autoactivation resulted in the fully processed active form of the enzyme. Aliquots of MMP-12 were stored at −70 C.

Determination of the Inhibition Constant ($K_i$) for MMP-12

The potency of inhibitors of MMP-12 was measured using either quartz cuvettes or microtiter plates. The activity of MMP-12 was measured using a fluorogenic substrate, Mca-Pro-Leu-Gly-Leu-Dpa-Ala-Arg-NH2, Knight, C. G. et al., *FEBS Lett.* 296,263–266 (1992), at 25 C. in an assay buffer containing 50 mM Tris, pH 7.6, 0.2 M sodium chloride, 50 mM calcium chloride, and 0.02% Brij-35. The increase in fluorescence due to cleavage of Gly-Leu peptide bond by MMP-12 was monitored with a Perkin-Elmer LS50B Fluorimeter ($\lambda$ex 328 nm, $\lambda$em 393 nm, excitation slit 2.5, emission slit 10) for the cuvette assay and with a Molecular Devices Fmax fluorescence plate reader ($\lambda$ex 320 nm, $\lambda\lambda$em 405 nm) for the microtiter plate assay. Substrate and inhibitor stock solutions were made in N,N, dimethylformamide (DMF) and 0.1% HCl-DMF, respectively.

Ki values were determined using the cuvette method by preparing a series of intermediate inhibitors solutions in 0.1% HCl-DMF and mixing the inhibitor with substrate (final concentration 2 $\mu$M) in a quartz cuvette containing 2 ml of assay buffer. MMP-12 was added to start the reaction at a concentration of 2 nM and progress curves were generated. For routine measurement of a Ki value for a reversible competitive inhibitor, the initial rates in the presence of at least four inhibitor concentrations (two concentrations above and two concentrations below the Ki) were measured [S]=2 $\mu$M (<<Km) and [MMP-12]=2 nM. Under these conditions, the measured Ki,app is close to the true Ki.

Ki values were determined using the microtiter plate method in a manner similar to that described for the cuvette method with some modifications. Four different inhibitor concentrations (50 $\mu$l in assay buffer)of each compound were added to separate wells of a microtiter plate and substrate was added (100 $\mu$l) to get a final concentration of 4 mM. MMP-12 was added to a final concentration of 2 nM (50 $\mu$l) to start the reaction. Cleavage of substrate was recorded every 30 seconds for 30 minutes and progress curves were generated.

Calculation of Ki Values

The Ki for a competitive inhibitor was calculated using: Vo/Vi=(1+[I]/Ki,app) and Ki=Ki,app/(1+[S]/Km), where Vo is the initial rate in the absence of inhibitor, Vi is the initial rate in the presence of inhibitor at the concentration of [I], [S] is the substrate concentration, and Km is the Michaelis constant. If slow binding is observed (i.e. if the approach to the binding equilibrium is slow), the final steady-state rate rather than the initial rate is taken as Vi.

What is claimed is:

1. A compound of the formula

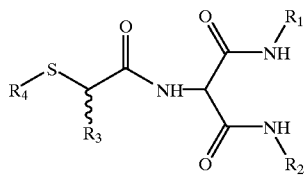

wherein $R_1$ and $R_2$ are each independently selected from the group consisting of hydrogen, $C_1$–$C_{10}$ alkyl, —(CH$_2$)$_a$—Ar$_1$, and —(CH$_2$)$_b$—Ar$_2$; wherein a is an integer from 1 to 6;
b is an integer from 2 to 6;

Ar$_1$ is a radical selected from the group consisting of

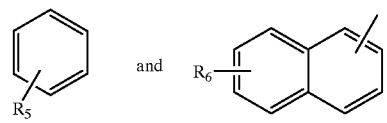

wherein $R_5$ is 1 or 2 substituents independently selected from the group consisting of hydrogen, halogen, $C_1$–$C_4$ alkyl, hydroxy, and $C_1$–$C_4$ alkoxy;

$R_6$ is selected from the group consisting of hydrogen, halogen, $C_1$–$C_4$ alkyl, and $C_1$–$C_4$ alkoxy;

Ar$_2$ is the radical

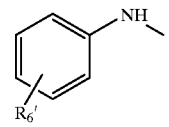

wherein $R_{6'}$ is selected from the group consisting of hydrogen, halogen, $C_1$–$C_4$ alkyl, and $C_1$–$C_4$ alkoxy;

$R_3$ is selected from the group consisting of $C_1$–$C_6$ alkyl, —(CH$_2$)$_p$—Ar$_3$, —(CH$_2$)$_k$—CO$_2$R$_9$, —(CH$_2$)$_m$—NR$_8$SO$_2$—Y$_1$, and —(CH$_2$)$_m$—Z—Q wherein m is an integer from 2 to 8;
p is an integer from 0–10;
k is an integer from 1 to 9;

Ar$_3$ is

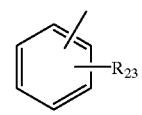

wherein $R_{23}$ is from 1 to 2 substituents independently selected from the group consisting of hydrogen, halogen, $C_1$–$C_4$ alkyl, and $C_1$–$C_4$ alkoxy;

$R_{8'}$ is hydrogen or $C_1$–$C_6$ alkyl;
$R_9$ is hydrogen or $C_1$–$C_6$ alkyl;

$Y_1$ is selected from the group consisting of hydrogen, —(CH$_2$)$_j$—Ar$_4$, and —N(R$_{24}$)$_2$ wherein j is 0 or 1;

$R_{24}$ each time selected is independently hydrogen or $C_1$–$C_6$ alkyl;

Ar$_4$ is the radical

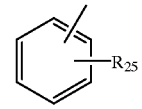

wherein $R_{25}$ is from 1 to 3 substituents independently selected from the group consisting of hydrogen, halogen, $C_1$–$C_4$ alkyl, and $C_1$–$C_4$ alkoxy;

Z is selected from the group consisting of —O—, —NR$_8$—, —C(O)NR$_8$—, —NR$_8$C(O)—, —NR$_8$C(O)NH—, —NR$_8$C(O)O—, and —OC(O)NH—; wherein $R_8$ is hydrogen or $C_1$–$C_6$ alkyl;

Q is selected from the group consisting of hydrogen, —$(CH_2)_n$—$Y_2$, and —$(CH_2)_x Y_3$; wherein n is an integer from 0 to 4;

$Y_2$ is selected from the group consisting of hydrogen, —$(CH_2)_h$—$Ar_5$ and —$(CH_2)_t$—$C(O)OR_{27}$ wherein $Ar_5$ is selected from the group consisting of

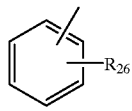

wherein $R_{26}$ is from 1 to 3 substituents independently selected from the group consisting of hydrogen, halogen, $C_1$–$C_4$ alkyl, and $C_1$–$C_4$ alkoxy;

h is an integer from 0 to 6;

t is an integer from 1 to 6;

$R_{27}$ is hydrogen or $C_1$–$C_6$ alkyl;

x is an integer from 2 to 4;

$Y_3$ is —$N(R_{28})_2$; wherein $R_{28}$ each time taken is independently hydrogen or $C_1$–$C_6$ alkyl;

$R_4$ is selected from the group consisting of hydrogen, —$C(O)R_{10}$, —$C(O)$—$(CH_2)_q$—K and —S—G wherein $R_{10}$ is selected from the group consisting of hydrogen, $C_1$–$C_4$ alkyl, phenyl, and benzyl;

q is 0, 1, or 2;

K is selected from the group consisting of

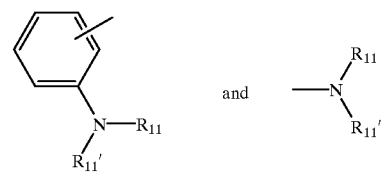

wherein $R_{11}$ is selected from the group consisting of hydrogen, $C_1$–$C_4$ alkyl, and benzyl;

$R_{11'}$ is selected from the group consisting of hydrogen, $C_1$–$C_4$ alkyl, and benzyl;

G is selected from the group consisting of

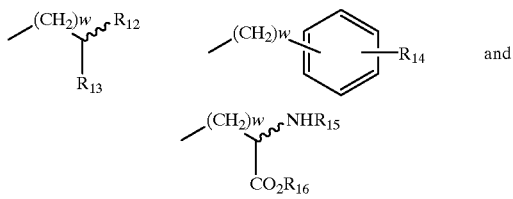

wherein w is an integer from 1 to 3;

$R_{12}$ is selected from the group consisting of hydrogen, $C_1$–$C_6$ alkyl, —$CH_2CH_2S(O)_eCH_3$, and benzyl; wherein e is 0, 1, or 2;

$R_{13}$ is selected from the group consisting of hydrogen, hydroxy, amino, $C_1$–$C_6$ alkyl, N-methylamino, N,N-dimethylamino, —$CO_2R_{17}$, and —$OC(O)R_{18}$; wherein $R_{17}$ is hydrogen, —$CH_2O$—$C(O)C(CH_3)_3$, $C_1$–$C_4$ alkyl, benzyl, or diphenylmethyl;

$R_{18}$ is hydrogen, $C_1$–$C_6$ alkyl or phenyl;

$R_{14}$ is 1 or 2 substituents independently selected from the group consisting of hydrogen, $C_1$–$C_4$ alkyl, $C_1$–$C_4$ alkoxy, or halogen;

$R_{15}$ is selected from the group consisting of hydrogen, $C_1$–$C_6$ alkyl and benzyl;

$R_{16}$ is selected from the group consisting of hydrogen and $C_1$–$C_4$ alkyl;

and stereoisomers, pharmaceutically acceptable salt, and hydrate thereof.

2. The compound according to claim 1 wherein $R_1$ and $R_2$ are both $C_1$–$C_6$ alkyl.

3. The compound according to claim 1 wherein $R_1$ and $R_2$ are both —$(CH_2)_a$—$Ar_1$ wherein a and $Ar_1$ are as defined in claim 1.

4. The compound according to claim 3 wherein a is 1 or 2.

5. The compound according to claim 3 wherein $Ar_1$ is phenyl or substituted phenyl.

6. The compound according to claim 1 wherein $R_4$ is hydrogen.

7. The compound according to claim 1 wherein $R_4$ is —S—G.

8. The compound according to claim 1 wherein $R_4$ is —$C(O)R_{10}$.

9. The comopund according to claim 8 wherein $R_{10}$ is $C_1$–$C_4$ alkyl.

10. The compound according to claim 1 which is N,N'-Diphenethyl-2-((S)-2-mercapto-3-methylbutyrylamino) malonamide.

11. The compound according to claim 1 which is N,N'-Diphenethyl-2-((S)-2-mercapto-3-phenylpropionylamino) malonamide.

12. The compound according to claim 1 which is N,N'-Diphenethyl-2-((S)-2-mercapto-4-phenylbutyrylamino) malonamide.

13. The compound according to claim 1 which is N,N'-Dibenzyl-2-((S)-2-mercapto-3-phenylpropionylamino) malonamide.

14. The compound according to claim 1 which is N,N'-Di-(3-phenylpropyl)-2-((S)-2-mercapto-3-phenylpropionylamino)malonamide.

15. The compound according to claim 1 which is N,N'-Di-(4-methoxyphenethyl)-2-((S)-2-mercapto-3-phenylpropionylamino)malonamide.

16. The compound according to claim 1 which is N,N'-Dipentyl-2-(2-mercapto-3-phenylpropionylamino) malonamide.

17. The compound according to claim 1 which is N,N'-Di-(2-(N-anilino)ethyl)-2-(2-mercapto-3-phenylpropionylamino)malonamide.

18. The compound according to claim 1 which is N,N'-Diphenethyl-2-((S)-2-mercaptopropionylamino) malonamide.

19. The compound according to claim 1 which is N,N'-Diphenethyl-2-(2-mercaptopropionylamino)malonamide.

20. The compound according to claim 1 which is N,N'-Diphenethyl-2-(2-mercaptopentanoylamino)malonamide.

21. The compound according to claim 1 which is N,N'-Di-(4-chlorophenethyl)-2-(2-mercapto-3-phenylpropionylamino)malonamide.

22. The compound according to claim 1 which is N,N'-Di-(2-methoxyphenethyl)-2-((S)-2-mercapto-3-phenylpropionylamino)malonamide.

23. The compound according to claim 1 which is N,N'-Di-(4-methylphenethyl)-2-((S)-2-mercapto-3-phenylpropionylamino)malonamide.

24. The compound according to claim 1 which is N,N'-Di-(3-methoxyphenethyl)-2-(2-mercapto-3-phenylpropionylamino)malonamide.

25. The compound according to claim 1 which is N,N'-Di-(3,4-dimethoxyphenethyl)-2-((S)-2-mercapto-3-phenylpropionylamino)malonamide.

26. The compound according to claim 1 which is N,N'-Di-(3-chlorophenethyl)-2-(2-mercapto-3-phenylpropionylamino)malonamide.

27. The compound according to claim 1 which is N,N'-Di-(3,4-dichlorophenethyl)-2-(2-mercapto-3-phenylpropionylamino)malonamide.

28. A pharmaceutical composition comprising an effective matrix metalloproteinase inhibiting amount of a compound of claim 1.

29. A method of inhibiting matrix metalloproteinase in a patient in need thereof comprising administering to the patient an effective matrix metalloproteinase inhibiting amount of a compound of claim 1.

30. A method of treating a neoplastic disease in a patient in need thereof comprising administering to the patient an effective matrix metalloproteinase inhibiting amount of a compound of claim 1.

31. A method of treating rheumatoid arthritis in a patient in need thereof comprising administering to the patient an effective matrix metalloproteinase inhibiting amount of a compound of claim 1.

32. A method of treating osteoporosis in a patient in need thereof comprising administering to the patient an effective matrix metalloproteinase inhibiting amount of a compound of claim 1.

33. A method of treating chronic inflammatory disorders in a patient in need thereof comprising administering to the patient an effective matrix metalloproteinase inhibiting amount of a compound of claim 1.

34. The method according to claim 33 wherein the chronic inflammatory disorder is emphysema.

* * * * *